(12) United States Patent
Zhang et al.

(10) Patent No.: US 11,970,502 B2
(45) Date of Patent: Apr. 30, 2024

(54) MACROCYCLIC ANTIVIRAL AGENTS

(71) Applicant: Enanta Pharmaceuticals, Inc., Watertown, MA (US)

(72) Inventors: Jiajun Zhang, Cambridge, MA (US); Xiaowen Peng, Sudbury, MA (US); Yat Sun Or, Waltham, MA (US)

(73) Assignee: Enanta Pharmaceuticals, Inc., Watertown, MA (US)

(*) Notice: Subject to any disclaimer, the term of this patent is extended or adjusted under 35 U.S.C. 154(b) by 0 days.

(21) Appl. No.: 17/735,203

(22) Filed: May 3, 2022

(65) Prior Publication Data
US 2022/0380377 A1 Dec. 1, 2022

Related U.S. Application Data

(60) Provisional application No. 63/183,977, filed on May 4, 2021.

(51) Int. Cl.
*C07D 487/08* (2006.01)
*C07D 498/18* (2006.01)

(52) U.S. Cl.
CPC ......... *C07D 487/08* (2013.01); *C07D 498/18* (2013.01)

(58) Field of Classification Search
CPC .. C07D 487/08; C07D 498/18; A61K 31/407; A61K 31/424
USPC ................. 540/460; 514/375, 414
See application file for complete search history.

(56) References Cited

U.S. PATENT DOCUMENTS

| | | | |
|---|---|---|---|
| 8,222,288 B2 | 7/2012 | Wang et al. |
| 8,222,425 B2 | 7/2012 | Britt et al. |
| 8,372,802 B2 | 2/2013 | Gai et al. |
| 9,290,757 B2 | 3/2016 | Madison |
| 9,309,284 B2 | 4/2016 | Chang et al. |
| 9,428,739 B2 | 8/2016 | Colt et al. |
| 9,474,759 B2 | 10/2016 | Chang et al. |
| 9,591,858 B2 | 3/2017 | Valles et al. |
| 9,828,342 B2 | 11/2017 | Home et al. |
| 9,975,885 B2 | 5/2018 | St. John et al. |
| 10,017,463 B2 | 7/2018 | Hedstrom et al. |
| 10,130,701 B2 | 11/2018 | Bickerton et al. |
| 10,590,084 B2 | 3/2020 | Buckman et al. |
| 10,934,261 B2 | 3/2021 | Buckman et al. |
| 10,959,969 B1 | 3/2021 | Johnson |
| 11,013,779 B2 | 5/2021 | Chang et al. |
| 11,021,513 B2 | 6/2021 | Schinazi et al. |
| 11,033,600 B2 | 6/2021 | Chang et al. |
| 11,045,546 B1 | 6/2021 | Kelly et al. |
| 11,058,763 B2 | 7/2021 | Zhang et al. |
| 11,058,779 B2 | 7/2021 | Lu et al. |
| 11,124,497 B1 | 9/2021 | Arnold et al. |
| 11,174,231 B1 | 11/2021 | Arnold et al. |
| 11,207,370 B2 | 12/2021 | Schinazi et al. |
| 11,319,325 B1 | 5/2022 | Zhang et al. |
| 11,325,916 B1 | 5/2022 | Shen et al. |
| 11,339,170 B1 | 5/2022 | Gao et al. |
| 11,352,363 B1 | 6/2022 | Wang et al. |
| 11,358,953 B2 | 6/2022 | Panarese et al. |
| 11,384,090 B2 | 7/2022 | Wang et al. |
| 2005/0143320 A1 | 6/2005 | Yang et al. |
| 2006/0014821 A1 | 1/2006 | He et al. |
| 2008/0125430 A1 | 5/2008 | Wang et al. |
| 2009/0137818 A1 | 5/2009 | Hilgenfeld et al. |
| 2010/0272681 A1 | 10/2010 | Farmer et al. |
| 2010/0317661 A1 | 12/2010 | Wang et al. |
| 2013/0072500 A1 | 3/2013 | Banka et al. |
| 2013/0072686 A1 | 3/2013 | Cadieux et al. |
| 2014/0148494 A1 | 5/2014 | Wang et al. |
| 2014/0243341 A1 | 8/2014 | Chang et al. |
| 2014/0378680 A1 | 12/2014 | Wang et al. |

(Continued)

FOREIGN PATENT DOCUMENTS

| CN | 114057624 A | 2/2022 |
| CN | 115894504 A | 4/2023 |

(Continued)

OTHER PUBLICATIONS

Pubchem, SID 160923150, deposited Mar. 4, 2013.

(Continued)

*Primary Examiner* — Jeffrey H Murray

(74) *Attorney, Agent, or Firm* — Edgar W. Harlan; Carolyn S. Elmore; Elmore Patent Law Group, P.C.

(57) ABSTRACT

The present invention discloses macrocyclic compounds of Formula (I), and pharmaceutically acceptable salts, thereof:

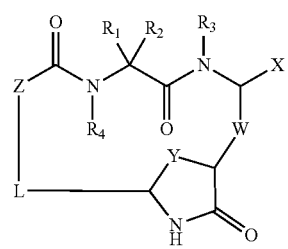

(I)

which inhibit coronavirus replication activity. The invention further relates to pharmaceutical compositions comprising a compound of Formula (I) or a pharmaceutically acceptable salt thereof, and methods of treating or preventing a coronavirus infection in a subject in need thereof, comprising administering to the subject a therapeutically effective amount of a compound of Formula (I) or a pharmaceutically acceptable salt thereof.

11 Claims, No Drawings

(56) References Cited

U.S. PATENT DOCUMENTS

| | | |
|---|---|---|
| 2015/0133368 A1 | 5/2015 | Chang et al. |
| 2015/0336928 A1 | 11/2015 | Fang et al. |
| 2016/0014821 A1 | 1/2016 | Toebes |
| 2017/0044183 A1 | 2/2017 | Lim et al. |
| 2018/0099981 A1 | 4/2018 | Estrada et al. |
| 2019/0161472 A1 | 5/2019 | Ombrato et al. |
| 2020/0230198 A1 | 7/2020 | Chang et al. |
| 2021/0355111 A1 | 11/2021 | Arnold et al. |
| 2022/0033383 A1 | 2/2022 | Panarese et al. |
| 2022/0041652 A1 | 2/2022 | Panarese et al. |
| 2022/0048944 A1 | 2/2022 | Panarese et al. |
| 2022/0162216 A1 | 5/2022 | Wang et al. |
| 2022/0162231 A1 | 5/2022 | Wang et al. |
| 2022/0380377 A1 | 12/2022 | Zhang et al. |
| 2022/0402926 A1 | 12/2022 | Zhang et al. |
| 2023/0103494 A1 | 4/2023 | Wang et al. |
| 2023/0115107 A1 | 4/2023 | Gao et al. |
| 2023/0122228 A1 | 4/2023 | Shen et al. |
| 2023/0151019 A1 | 5/2023 | Cao et al. |
| 2023/0159545 A1 | 5/2023 | Panarese et al. |
| 2023/0159546 A1 | 5/2023 | Kass et al. |
| 2023/0174531 A1 | 6/2023 | Panarese et al. |
| 2023/0203048 A1 | 6/2023 | Wang et al. |

FOREIGN PATENT DOCUMENTS

| | | |
|---|---|---|
| GB | 2595975 A | 12/2021 |
| WO | 0059929 A1 | 10/2000 |
| WO | 0208244 A2 | 1/2002 |
| WO | 2004101742 A3 | 6/2005 |
| WO | 2005113580 A1 | 12/2005 |
| WO | 2006061714 A3 | 8/2006 |
| WO | 2007038138 A2 | 4/2007 |
| WO | 2008144507 A2 | 11/2008 |
| WO | 2012099454 A1 | 7/2012 |
| WO | 2013049382 A3 | 5/2013 |
| WO | 2013166319 A1 | 11/2013 |
| WO | 2017222935 A1 | 12/2017 |
| WO | 2018023054 A1 | 2/2018 |
| WO | 2018042343 A2 | 3/2018 |
| WO | 2019086141 A1 | 5/2019 |
| WO | 2019086142 A1 | 5/2019 |
| WO | 2020081636 A1 | 4/2020 |
| WO | 2021205296 A1 | 10/2021 |
| WO | 2021206876 A1 | 10/2021 |
| WO | 2021206877 A1 | 10/2021 |
| WO | 2021207409 A2 | 10/2021 |
| WO | 2021226546 A1 | 11/2021 |
| WO | 2021250648 A1 | 12/2021 |
| WO | 2021252491 A1 | 12/2021 |
| WO | 2021252644 A1 | 12/2021 |
| WO | 2022013684 A1 | 1/2022 |
| WO | 2022020242 A1 | 1/2022 |
| WO | 2022020711 A1 | 1/2022 |
| WO | 2022109363 A1 | 5/2022 |

OTHER PUBLICATIONS

Pubchem, SID 267351747, deposited Dec. 11, 2015.
Pubchem, SID 367622864, May 25, 2018.
Anonymous, "Nirmatrelvir", Cortellis Database, Retrieved from the Internet: URL:https://www.cortellis.com/drugdiscovery/entity/drug/1126756/product?ent=qR5ruNw5&updateHistoryPage=5&orderBy=_score:desc, Nov. 8, 2022, 3 pgs.
Anonymous, "Pfizer Initiates Phase 1 Study of Novel Oral Antiviral Therapeutic Agent Against SARS-COV-2 Science Products Stories Newsroom About", Retrieved from the Internet: URL:https://www.pfizer.com/news/press-release/press-release-detail/pfizer-initiatesphase-1-study-novel-oral-antiviral [retrieved on Nov. 11, 2022], 9 pgs.
Chia, C.S. B. "Novel Coronavirus Main Protease Di- and Tripeptide Inhibitors for Treating COVID-19", ACS Med. Chem. Lett., 13(9), URL:https://pubs.acs.org/doi/pdf/10.1021/acsmedchemlett.2c00332, Aug. 8, 2022, 1388- 1389.
Chuck, C-P et al., "Design, synthesis and crystallographic analysis of nitrile-based broad-spectrum peptidomimetic inhibitors for coronavirus 3C-like proteases", Euro. J. Med. Chem., 59, https://doi.org/10.1016/j.ejmech.2012.10.053, Jan. 2013, 1-6.
Efremov, I. et al., "Discovery and Optimization of a Novel Spiropyrrolidine Inhibitor of B-Secretase (BACE1) through Fragment-Based Drug Design", J. Med. Chem., vol. 55, Apr. 2, 2012, 9069-9088.
Halford, B. "Pfizer unveils its oral SARS-00V-2 inhibitor—The antiviral candidate is the first orally administered compound to enter clinical trials that targets the virus's main protease", Chem. & Eng. News, online at https://cen.acs.org/acs-news/acs-meeting-news/Pfizer-unveils-oral-SARS-CoV/99/i13, (a version appeared in 99(13)), Apr. 7, 2021, 2 pgs.
Halford, B. "Pfizer's novel COVID-19 antiviral heads to clinical trials—The small molecule targets coronavirus 3CL protease and is active against multiple coronaviruses in cell studies", Chem. & Eng. News, online at https://cen.acs.org/pharmaceuticals/drug-discovery/Pfizers-novel-COVID-19-antiviral/98/web/2020/09, Sep. 17, 2020, 2 pgs.
Kelemen, A. et al., "Spiro[pyrrolidine-3,3'-oxindoles] and Their Indoline Analogues as New 5-HT6 Receptor Chemotypes", Molecules, vol. 22, DOI: 10.3390/molecules22122221, Dec. 14, 2017, 1-25.
Konno, S. et al., "3CL Protease Inhibitors with an Electrophilic Arylketone Moiety as Anti-SARS-CoV-2 Agents", J. Medicinal Chemistry, https://doi.org/10.1021/acs.jmedchem.1c00665, Jul. 27, 2021, pp. 1-14.
Lee., C. et al., "Structural Basis of Inhibition Specificities of 3C and 3C-like Proteases by Zinc-coordinating and Peptidomimetic Compounds", J. Biological Chem., 284(12), Mar. 20, 2009, 7646-7655.
Mandadapu, S. et al., "Macrocyclic Inhibitors of 3c and 3C-Like Proteases of Picornavirus, Norovirus, and Coronavirus", Bioorg. & Med. Chem. Lett., 23, http:lfdx.doi.org/10.1016/j.bmcl.2013.05.021, May 16, 2013, 3709-3712.
Owen, D. "Oral inhibitors of the 1-12 SARS-CoV-2 main protease for the treatment of COVID-19", 261ST Am. Chem. Soc. (ACS) Natl Meet, Apr. 16, 2021, 1 pg.
Thanigaimalai, P. et al., "Design, synthesis, and biological evaluation of novel dipeptide-type SARS-CoV 3CL protease inhibitors: Structure-activity relationship study", Euro J. Med. Chem., 65, DOI: 10.1016/J.EJMECH.2013.05.005, May 20, 2013, 436-447.
Wang, Y. et al., "Inhibition of Enterovirus 71 Replication by an a-Hydroxy-Nitrile Derivative NK-1.9k", Antiviral Res., 141, Jan. 5, 2017, 91-100.
Xu, J. et al., "Green Oxidation of Indoles Using Halide Catalysis", Nature Communications, 10:4754, https://doi.org/10.1038/s41467-019-12768-4, Oct. 18, 2019, 1-11.
Yang, S. et al., "Synthesis, Crystal Structure, Structure-Activity Relationships, and Antiviral Activity of a Potent SARS Coronavirus 3CL Protease Inhibitor", J. Med. Chem., 49, Jul. 14, 2006, 4971-4980.
Zhang, L. et al., "a-Ketoamides as Broad-Splectrum Inhibitors of Coronavirus and Enterovirus Replication: Structue-Based Design, Synthesis, and Activity Assessment", J. Med. Chem., 63, https://dx.doi.org/10.1021/acs,jmedchem.9b01828, 2020, 4562-4578.
Zhou, L. et al., "An Overview of Spirooxindole as a Promising Scaffold for Novel Drug Discovery", Expert Opinion on Drug Discovery, 15(5), Feb. 2020, 603-625.
Panarese, Joseph D. et al., U.S. Appl. No. 18/102,850, filed Jan. 30, 2023.
Pubchem, SID 326247498, deposited Jan. 25, 2017.
"1-(2-oxospiro[1H-indole-3,3'-pyrrolidine]-1'-yl)-4-pyridin-2-ylbutane-1,4-dione", Pubchem CID 145894940. Create Date: Feb. 12, 2020. Date Accessed: Jun. 9, 2023, 2 pgs.
Bafna, K., et al., "Structural Similarity of SARS-CoV2 Mpro and HCV NS3/4A Proteases Suggests New Approaches for Identifying Existing Drugs Useful as COVID-19 Therapeutics", , ChemRxiv online at DOI: 10.26434/chem rxiv.12153615. v1.
Baker, J. D, et al., "A drug repurposing screen identifies hepatitis C antivirals as inhibitors of the SARS-CoV-2 main 1 protease", BioRxiv. Preprint. avail at https://doi.org/10.1101/2020.07.10.197889, Jul. 10, 2020.

(56) References Cited

OTHER PUBLICATIONS

Dai, W., et al., "Structure-based design of antiviral drug candidates targeting the SARS-CoV-2 main protease", Science, 368(6497)DOI: 10.1126/science. abb4489, 1331-1334.

Marti, C., "Novel Approach to Spiro-Pyrrolidine-Oxindoles and its Application to the Synthesis of (+-)-Horsfiline and (−)-Spirotryprostatin", ETH Library, Doctoral Thesishttps://doi.org/10.3929/ethz-a-004489068, 1-2, 23-25.

Vandyck, K., et al., "Considerations for the discovery and development of 3-chymotrypsin-like cysteine protease inhibitors targeting SARS-CoV-2 infection", Current opinion in virology, 49DOI: 10.1016/j.coviro.2021.04.006, 36- 40.

Ziarani, G, et al., "Synthesis of Spiro-Fused Heterocyclic Scaffolds Through Multicomponent Reactions Involving Isatin", ARKIVOC, 2016 (i)http://dx.doi.org/10.3998/ark.5550190.p009.385, 1, 14-16.

MACROCYCLIC ANTIVIRAL AGENTS

RELATED APPLICATION

This application claims the benefit of U.S. Provisional Application No. 63/183,977, filed on May 4, 2021. The entire teachings of the above application are incorporated herein by reference.

TECHNICAL FIELD

The invention relates to compounds and methods of inhibiting coronavirus replication activity by contacting the 3C-Like protease (sometimes referred to as "3CLpro", "Main protease", or "Mpro") with a therapeutically effective amount of a 3C-Like protease inhibitor. The invention further relates to pharmaceutical compositions containing the coronavirus 3C-Like protease inhibitor in a mammal by administering effective amounts of such coronavirus 3C-Like protease inhibitor.

BACKGROUND OF THE INVENTION

Coronaviruses are enveloped, positive-sense, single-stranded RNA viruses. The genomic RNA of CoVs has a 5'-cap structure and 3'-poly-A tail and contains at least 6 open reading frames (ORFs). The first ORF (ORF 1a/b) directly translates two polyproteins: pp1a and pp1ab. These polyproteins are processed by a 3C-Like protease (3CLpro), also known as the main protease (Mpro), into 16 non-structural proteins. These non-structural proteins engage in the production of subgenomic RNAs that encode four structural proteins, namely envelope, membrane, spike, and nucleocapsid proteins, among other accessory proteins. As a result, it is understood that 3C-Like protease has a critical role in the coronavirus life cycle.

3CLpro is a cysteine protease involved in most cleavage events within the precursor polyprotein. Active 3CLpro is a homodimer containing two protomers and features a Cys-His dyad located in between domains I and II. 3CLpro is conserved among coronaviruses and several common features are shared among the substrates of 3CLpro in different coronaviruses. As there is no human homolog of 3CLpro, it is an ideal antiviral target. Although compounds have been reported to inhibit 3CLpro activity, they have not been approved as coronavirus therapies. (Refer to WO 2004101742 A2, US 2005/0143320 A1, US 2006/0014821 A1, US 2009/0137818 A1, WO 2013/049382 A2, WO 2013/166319 A1, WO2018042343, WO2018023054, WO2005113580, and WO2006061714).

More effective therapies for coronavirus infections are needed due to this high unmet clinical need. This invention provides compounds which inhibit the coronavirus lifecycle and methods for preparation and use of these compounds. These compounds are useful for treating or preventing coronavirus infections and decreasing occurrence of disease complications such as organ failure or death.

SUMMARY OF THE INVENTION

The present invention relates to novel antiviral compounds, pharmaceutical compositions comprising such compounds, as well as methods to treat or prevent viral (particularly coronavirus) infection in a subject in need of such therapy with said compounds. Compounds of the present invention inhibit the protein(s) encoded by a coronavirus or interfere with the life cycle of a coronavirus and are also useful as antiviral agents. In addition, the present invention provides processes for the preparation of said compounds.

The present invention provides compounds represented by Formula (I), and pharmaceutically acceptable salts, esters and prodrugs thereof,

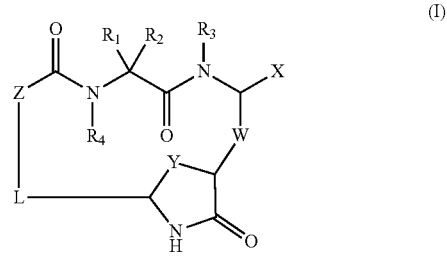

wherein:
X is selected from the group consisting of —CN, —C(O)$R_{11}$, —CH(OH)SO$_3$$R_{12}$, —C(O)NR$_{13}$R$_{14}$, —C(O)C(O)NR$_{13}$R$_{14}$, —C≡CR$_{13}$, —CH=CH—C(O)R$_{15}$, —CH=CH—C(O)OR$_{15}$, —CH=CH—C(O)NR$_{13}$R$_{14}$, —CH=CH—S(O)$_2$NR$_{13}$R$_{14}$, and —B(OR$_{13}$)$_2$;

$R_{11}$ is hydrogen or optionally substituted —C$_1$-C$_8$ alkyl;

$R_{12}$ is hydrogen or Na$^+$;

$R_{13}$ and $R_{14}$ at each occurrence are independently selected from the group consisting of hydrogen, optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocycloalkyl, optionally substituted aryl, optionally substituted arylalkyl, optionally substituted heteroaryl, optionally substituted heteroarylalkyl; alternatively $R_{13}$ and $R_{14}$ are taken together with the nitrogen atom to which they are attached to form an optionally substituted 3- to 8-membered heterocyclic ring;

$R_{15}$ is selected from the group consisting of optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocycloalkyl, optionally substituted aryl, optionally substituted arylalkyl, optionally substituted heteroaryl, and optionally substituted heteroarylalkyl;

Y is selected from the group consisting of absent, —CR$_{16}$R$_{17}$—, —(CR$_{16}$R$_{17}$)$_2$—, —CR$_{16}$R$_{17}$O— and —CR$_{16}$R$_{17}$NR$_{13}$—;

$R_{16}$ and $R_{17}$ at each occurrence are independently selected from the group consisting of: hydrogen, halogen, optionally substituted —C$_1$-C$_8$ alkyl, optionally substituted —C$_2$-C$_8$ alkenyl, optionally substituted —C$_2$-C$_8$ alkynyl, optionally substituted —C$_1$-C$_8$ alkoxy, optionally substituted —C$_3$-C$_8$ cycloalkyl, optionally substituted 3- to 8-membered heterocycloalkyl, optionally substituted aryl, optionally substituted arylalkyl, optionally substituted heteroaryl, and optionally substituted heteroarylalkyl;

W is selected from the group consisting of absent, —O—, —NR$_{13}$—, —CR$_{16}$R$_{17}$—, —(CR$_{16}$R$_{17}$)$_2$—, —CR$_{16}$R$_{17}$O—, and —CR$_{16}$R$_{17}$N(R$_{13}$)—;

$R_1$ is selected from the group consisting of optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocycloalkyl, optionally substituted aryl, optionally substituted arylalkyl, optionally substituted heteroaryl, and optionally substituted heteroarylalkyl;

R₂ is selected from the group consisting of hydrogen, fluorine, optionally substituted —C₁-C₆ alkyl, and optionally substituted —C₃-C₆ cycloalkyl;

Alternatively, R₁ and R₂ are taken together with the carbon atom to which they are attached to form an optionally substituted 3- to 6-membered cyclic alkyl ring or heterocyclic ring;

R₃ and R₄ are each independently selected from the group consisting of hydrogen, optionally substituted —C₁-C₈ alkyl, optionally substituted —C₂-C₈ alkenyl, optionally substituted —C₂-C₈ alkynyl, optionally substituted —C₃-C₈ cycloalkyl, optionally substituted 3- to 8-membered heterocycloalkyl, optionally substituted aryl, optionally substituted arylalkyl, optionally substituted heteroaryl, and optionally substituted heteroarylalkyl;

Alternatively, R₁ and R₄ are taken together with the carbon atom and nitrogen atom to which they are accordingly attached to form an optionally substituted heterocyclic ring;

Z is selected from the group consisting of —O—, —NR₁₃—, and —CR₂₁R₂₃—;

Alternatively, Z and the oxygen atom of the adjacent carbonyl group are taken together with the carbon atom to which they are attached to form an optionally substituted heteroaryl;

L is —Rₐ-Q-R_b—, wherein R_b is connected to Z;

Rₐ and R_b are independently selected from the group consisting of a direct bond, optionally substituted —C₁-C₈ alkyl, optionally substituted —C₂-C₈ alkenyl, optionally substituted —C₂-C₈ alkynyl, optionally substituted —C₃-C₈ cycloalkyl, optionally substituted 3- to 8-membered heterocycloalkyl, optionally substituted arylalkyl, and optionally substituted heteroarylalkyl;

When (i) R_b is not a direct bond or (ii) R_b is a direct bond and Z is —CR₂₁R₂₃—, Q is selected from the group consisting of —CR₂₁=CR₂₂—, —CR₂₁R₂₃—CR₂₂R₂₄—, —CR₂₁R₂₃C(O)—, —NR₁₃C(O)—, —NR₁₃C(O)O—, —NR₁₃C(O)NR₁₄—, —O—, —S—, —S(O)—, —S(O)₂—, —S(O)(NH)—, —N(R₁₅)—, optionally substituted aryl, optionally substituted heteroaryl, optionally substituted —C₃-C₈ cycloalkyl, and optionally substituted 3- to 8-membered heterocycloalkyl;

When R_b is a direct bond, and Z is —O— or —NR₁₃—, Q is selected from the group consisting of —CR₂₁=CR₂₂—, —CR₂₁R₂₃—CR₂₂R₂₄—, —CR₂₁R₂₃C(O)—, optionally substituted aryl, optionally substituted heteroaryl, optionally substituted —C₃-C₈ cycloalkyl, and optionally substituted 3- to 8-membered heterocycloalkyl;

R₁₈ is selected from the group consisting of hydrogen, optionally substituted —C₁-C₈ alkyl, optionally substituted —C₂-C₈ alkenyl, optionally substituted —C₂-C₈ alkynyl, optionally substituted —C₃-C₈ cycloalkyl, optionally substituted 3- to 8-membered heterocycloalkyl, optionally substituted aryl, optionally substituted arylalkyl, optionally substituted heteroaryl, optionally substituted heteroarylalkyl, —C(O)R₁₅, —C(O)OR₁₅, —C(O)NR₁₃R₁₄, —C(O)C(O)NR₁₃R₁₄, —S(O)₂R₁₅, and —S(O)₂NR₁₃R₁₄;

R₂₁ and R₂₂ at each occurrence are independently selected from the group consisting of: hydrogen, halogen, optionally substituted —C₁-C₆ alkyl, and optionally substituted —C₃-C₈ cycloalkyl; preferable R₂₁ and R₂₂ at each occurrence are each independently selected from hydrogen, fluorine, optionally substituted methyl and optionally substituted cyclopropyl, and R₂₃ and R₂₄ at each occurrence are independently selected from the group consisting of: hydrogen, halogen, —OH, —OR₁₅, —OC(O)R₁₅, —OC(O)OR₁₅, —OC(O)NR₁₃R₁₄, —NR₁₃R₁₅, —N₃, —CN, optionally substituted —C₁-C₈ alkyl, optionally substituted —C₂-C₈ alkenyl, optionally substituted —C₂-C₈ alkynyl, optionally substituted —C₃-C₈ cycloalkyl, optionally substituted 3- to 8-membered heterocycloalkyl, optionally substituted aryl, optionally substituted arylalkyl, optionally substituted heteroaryl, and optionally substituted heteroarylalkyl.

DETAILED DESCRIPTION OF THE INVENTION

In one embodiment of the present invention is a compound of Formula (I) as described above, or a pharmaceutically acceptable salt thereof.

In certain embodiments of the compounds of Formula (I), R₁ is optionally substituted —C₁-C₄ alkyl, optionally substituted —C₃-C₆ cycloalkyl; optionally substituted aryl, optionally substituted arylalkyl, or optionally substituted heteroarylalkyl; and R₂ is hydrogen or fluorine.

In certain embodiments of the compounds of Formula (I), R₁ is selected from the following groups:

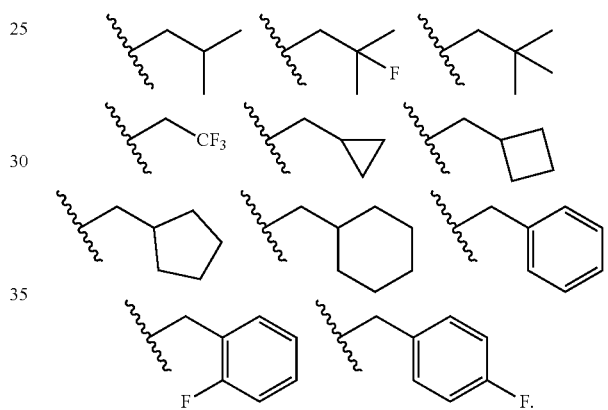

In certain embodiments of the compounds of Formula (I), R₁ is isobutyl.

In certain embodiments of the compounds of Formula (I), R₂ is hydrogen.

In certain embodiments of the compounds of Formula (I), R₃ is hydrogen, optionally substituted methyl, or optionally substituted cyclopropyl.

In certain embodiments of the compounds of Formula (I), R₃ is hydrogen, -Me, —CF₃ or cyclopropyl. In certain embodiments of the compounds of Formula (I), R₃ is hydrogen.

In certain embodiments of the compounds of Formula (I), R₄ is hydrogen, optionally substituted methyl, or optionally substituted cyclopropyl.

In certain embodiments of the compounds of Formula (I), R₄ is hydrogen, -Me, -Et, —Pr, -i-Pr, -allyl, —CF₃, —CD₃, or cyclopropyl. In certain embodiments of the compounds of Formula (I), R₄ is hydrogen or -Me.

In certain embodiments of the compounds of Formula (I), R₁ is optionally substituted isobutyl or optionally substituted cyclopropyl; R₂ is hydrogen or fluorine; R₃ is hydrogen or optionally substituted methyl; and R₄ is hydrogen or optionally substituted methyl.

In certain embodiments of the compounds of Formula (I), R₁ is isobutyl, R₂ is hydrogen, R₃ is hydrogen, and R₄ is methyl.

In certain embodiments of the compounds of Formula (I), X is —C(O)C(O)NR$_{13}$R$_{14}$, wherein R$_{13}$ and R$_{14}$ are previously defined.

In certain embodiments of the compounds of Formula (I), X is —C≡CR$_{13}$, wherein R$_{13}$ is previously defined.

In certain embodiments of the compounds of Formula (I), X is selected from the following:

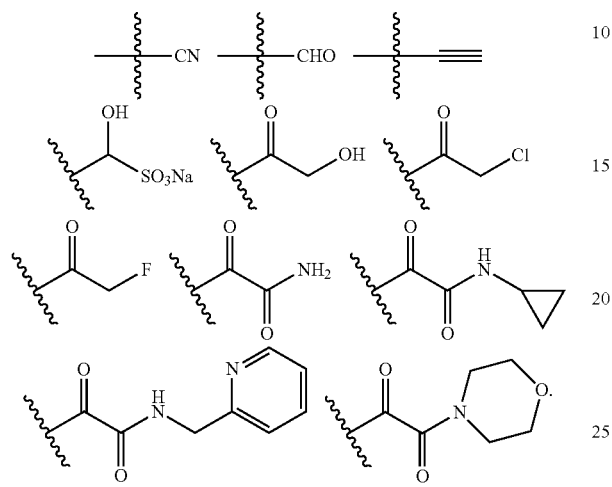

In certain embodiments of the compounds of Formula (I), X is —CN.

In certain embodiments of the compounds of Formula (I), Y is —CH$_2$—.

In certain embodiments of the compounds of Formula (I), W is —CH$_2$—.

In certain embodiments of the compounds of Formula (I), Y is —CH$_2$— and W is —CH$_2$—.

In certain embodiments of the compounds of Formula (I), Z is —CR$_{21}$R$_{23}$—.

In certain embodiments of the compounds of Formula (I), Z is

wherein A is selected from the group consisting of —R$_{15}$, —OR$_{15}$, —NR$_{13}$R$_{14}$, and —C(O)NR$_{13}$R$_{14}$; and R$_{13}$, R$_{14}$, R$_{15}$, and R$_{21}$ are previously defined. Preferably, A is optionally substituted —C$_1$-C$_8$ alkyl, optionally substituted aryl or optionally substituted heteroaryl. In certain embodiments, A is selected from the following groups, and is optionally substituted:

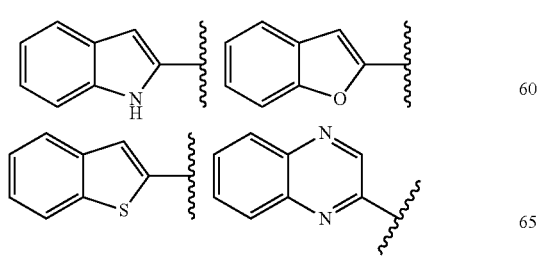

-continued

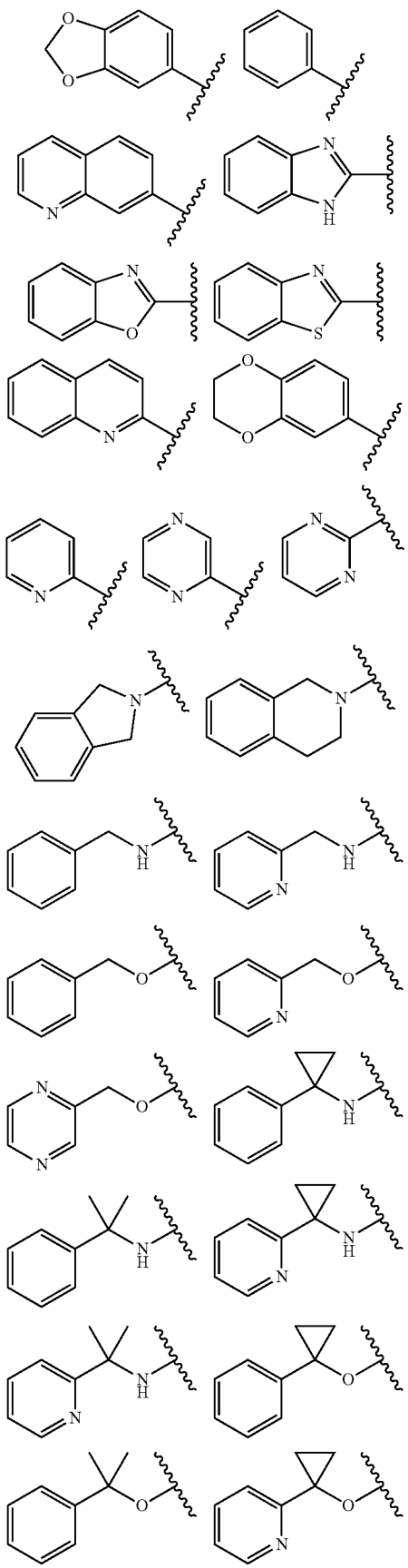

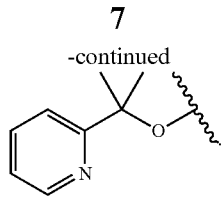

In certain embodiments of the compounds of Formula (I), L is —CR$_{21}$=CR$_{22}$— or —CR$_{21}$R$_{23}$—CR$_{22}$R$_{24}$—.

In certain embodiments of the compounds of Formula (I), L is —CH$_2$—CH$_2$—CH$_2$—CH$_2$— or —CH$_2$—CH=CH—CH$_2$—.

In certain embodiments, the compound of Formula (I) is represented by Formula (II):

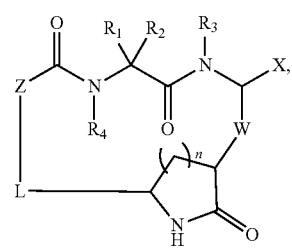

(II)

wherein n is 1 or 2; X, W, Z, L, R$_1$, R$_2$, R$_3$, and R$_4$ are as previously defined.

In certain embodiments, the compound of Formula (I) is represented by Formula (III):

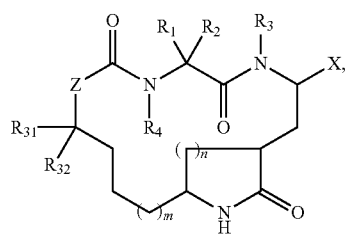

(III)

wherein m is 0, 1, 2, 3, 4, or 5; n, X, Z, R$_1$, R$_2$, R$_3$, and R$_4$ are as previously defined. Preferably, m is 1. R$_{31}$ and R$_{32}$ are each independently selected from the group consisting of: hydrogen, halogen, optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocycloalkyl, optionally substituted aryl, optionally substituted arylalkyl, optionally substituted heteroaryl, and optionally substituted heteroarylalkyl; alternatively R$_{31}$ and R$_{32}$ are taken together with the carbon atom to which they are attached to form an optionally substituted 3- to 8-membered carbocyclic or heterocyclic. In certain embodiments, R$_{31}$ and R$_{32}$ are both hydrogen.

In certain embodiments, the compound of Formula (I) is represented by one of Formulae (IV-1)~(IV-4):

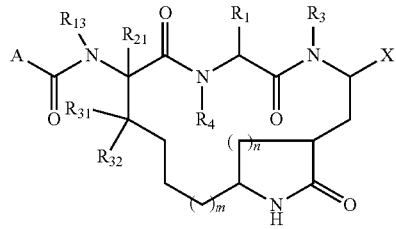

(IV-1)

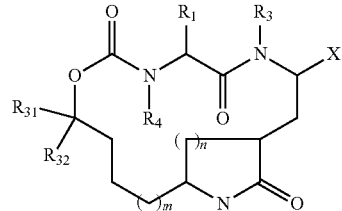

(IV-2)

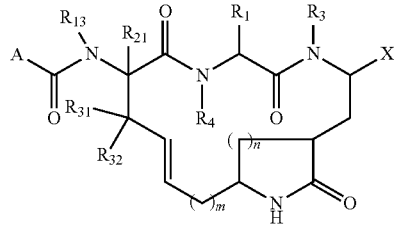

(IV-3)

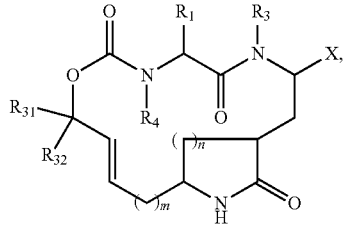

(IV-4)

wherein A, X, R$_1$, R$_3$, R$_4$, R$_{13}$, R$_{31}$, R$_{32}$, m, and n are as previously defined.

In certain embodiments, the compound of Formula (I) is represented by one of Formulae (IV-1) to (IV-4), wherein R$_{13}$ is hydrogen; R$_{21}$ is hydrogen; n is 1; R$_1$ is selected from the following:

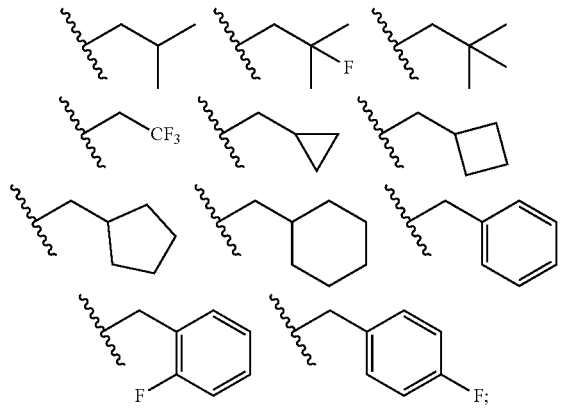

$R_3$ is hydrogen, -Me, —$CF_3$, or cyclopropyl; $R_4$ is hydrogen, -Me, -Et, —Pr, -i-Pr, -allyl, —$CF_3$, —$CD_3$, or cyclopropyl; and X is selected from the following:

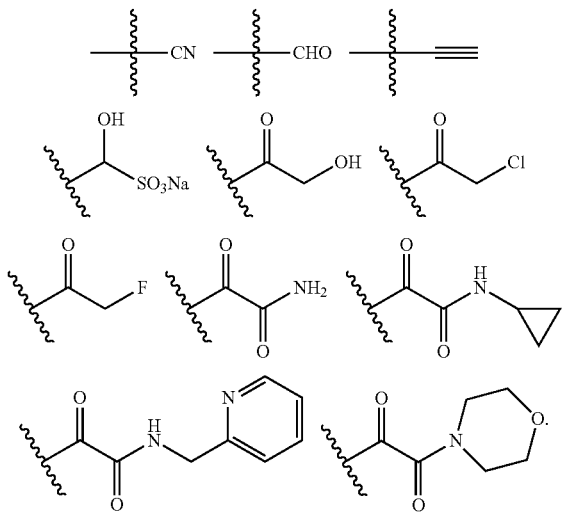

In certain embodiments, the compound of Formula (I) is represented by one of Formulae (V-1)~(V-4):

(V-1)
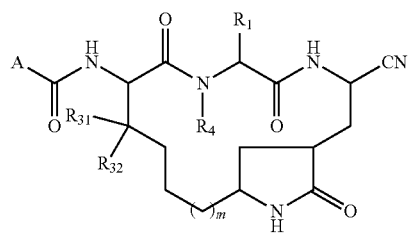

(V-2)
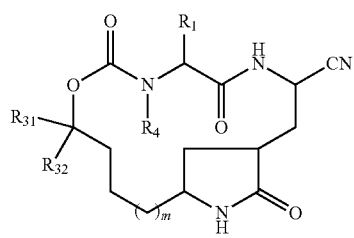

(V-3)
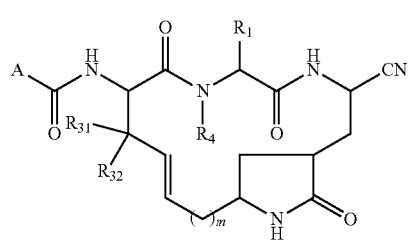

(V-4)
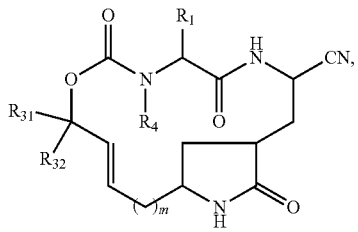

wherein A, $R_1$, $R_4$, $R_{31}$, $R_{32}$, and m are as previously defined.

In certain embodiments, the compound of Formula (I) is represented by one of Formulae (V-1a)~(V-4a):

(V-1a)
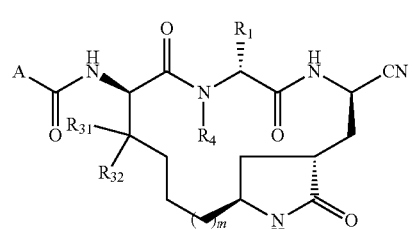

(V-2a)
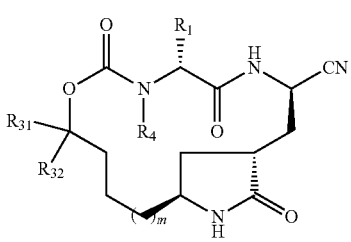

(V-3a)
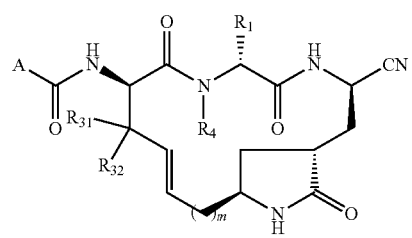

(V-4a)
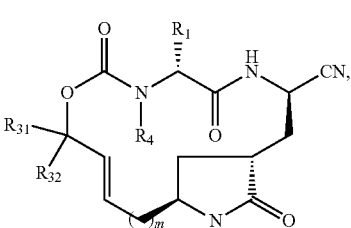

wherein A, $R_1$, $R_4$, $R_{31}$, $R_{32}$ and m are as previously defined.

In certain embodiments, the compound of Formula (I) is represented by one of Formulae (VI-1)~(VI-4):

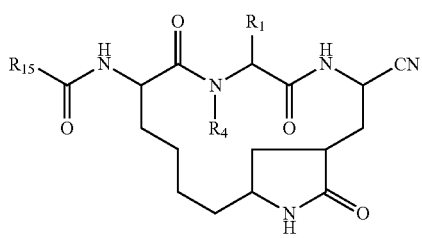
(VI-1)

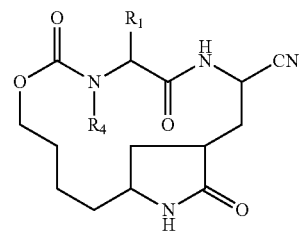
(VI-2)

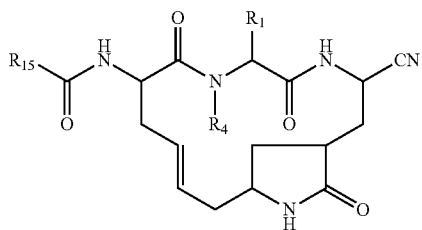
(VI-3)

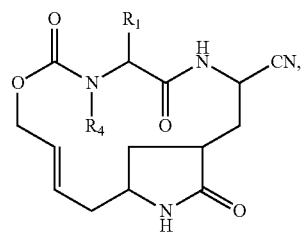
(VI-4)

wherein $R_1$, $R_4$, and $R_{15}$ are as previous defined.

In certain embodiments, the compound of Formula (I) is represented by one of Formulae (VI-1a)~(VI-4a):

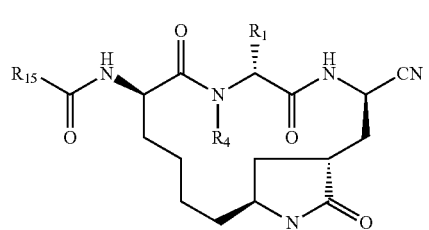
(VI-1a)

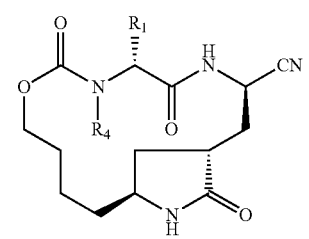
(VI-2a)

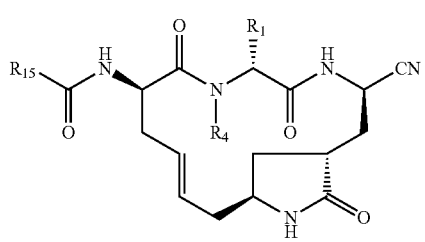
(VI-3a)

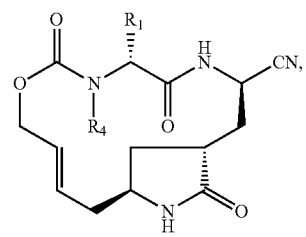
(VI-4a)

wherein $R_1$, $R_4$, and $R_{15}$ are as previously defined. In certain embodiments, the compound of Formula (I) is represented by one of Formulae (VII-1) and (VII-2):

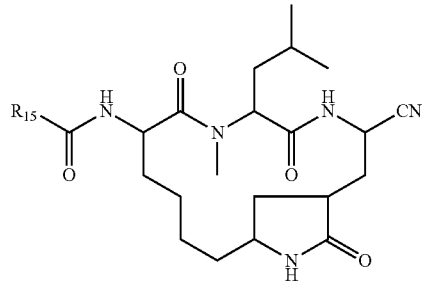
(VII-1)

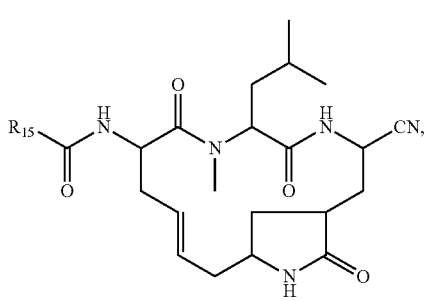
(VII-2)

wherein $R_{15}$ is as previously defined.

In certain embodiments, the compound of Formula (I) is represented by one of Formulae (VII-1a) and (VII-2a):

(VII-1a)

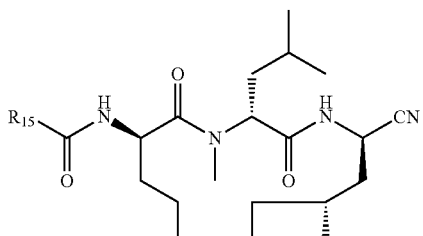

(VII-2a)

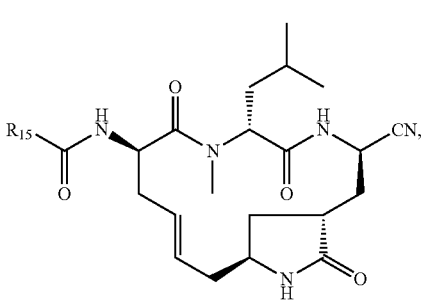

wherein $R_{15}$ is as previously defined.

In certain embodiments, the compound of Formula (I) is represented by one of Formula (VIII-1) and (VIII-2):

(VIII-1)

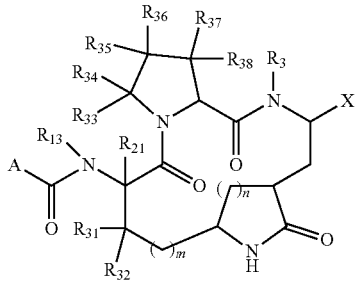

(VIII-2)

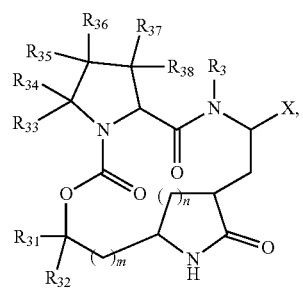

wherein X, A, $R_3$, $R_{13}$, $R_{31}$, $R_{32}$, m, and n are as previously defined. Preferably, m is 3. $R_{33}$, $R_{34}$, $R_{35}$, $R_{36}$, $R_{37}$ and $R_{38}$ are each independently selected from the group consisting of hydrogen, halogen, —OH, —$OR_{15}$, —CN, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, and optionally substituted heteroarylalkyl, wherein $R_{15}$ is as previously defined.

Alternatively, $R_{33}$ and $R_{34}$ are taken together with the carbon atom to which they are attached to form an optionally substituted 3- to 8-membered spiro cycloalkyl ring or heterocyclic ring.

Alternatively, $R_{35}$ and $R_{36}$ are taken together with the carbon atom to which they are attached to form an optionally substituted 3- to 8-membered spiro cycloalkyl ring or heterocyclic ring.

Alternatively, $R_{37}$ and $R_{38}$ are taken together with the carbon atom to which they are attached to form an optionally substituted 3- to 8-membered spiro cycloalkyl ring or heterocyclic ring.

Alternatively, $R_{34}$ and $R_{35}$ are taken together with the carbon atoms to which they are attached to form an optionally substituted 3- to 8-membered fused cycloalkyl ring or heterocyclic ring.

Alternatively, $R_{36}$ and $R_{37}$ are taken together with the carbon atoms to which they are attached to form an optionally substituted 3- to 8-membered fused cycloalkyl ring or heterocyclic ring.

In certain embodiments, the compound of Formula (I) is represented by one of Formulae (VIII-1) and (VIII-2), wherein $R_{13}$ is hydrogen; $R_{21}$ is hydrogen; n is 1; $R_3$ is hydrogen, -Me, —$CF_3$, or cyclopropyl; and X is selected from the following:

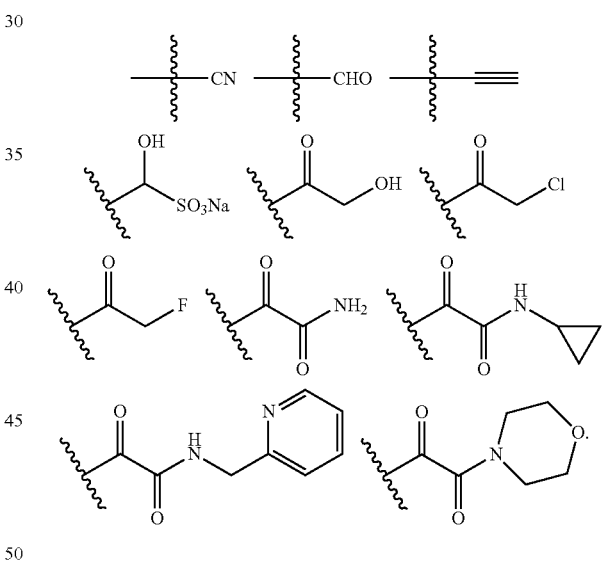

In certain embodiments, the compound of Formula (I) is represented by one of Formulae (IX-1) and (IX-2):

(IX-1)

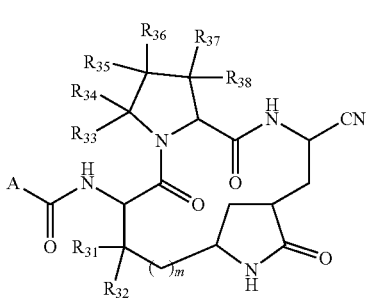

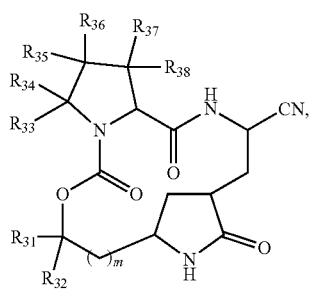

(IX-2)

wherein A, $R_{31}$, $R_{32}$, $R_{33}$, $R_{34}$, $R_{35}$, $R_{36}$, $R_{37}$, $R_{38}$, and m are as previously defined.

In certain embodiments, the compound of Formula (I) is represented by one of Formulae (IX-1a) and (IX-2a):

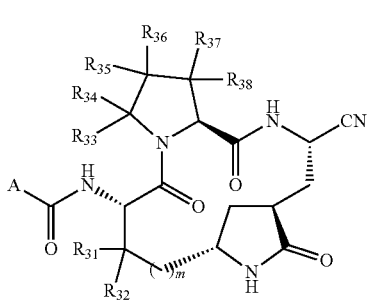

(IX-1a)

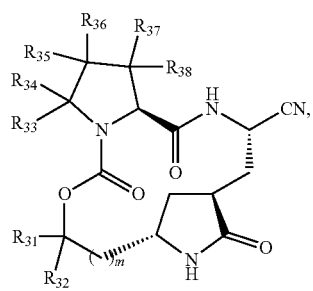

(IX-2a)

wherein A, $R_{31}$, $R_{32}$, $R_{33}$, $R_{34}$, $R_{35}$, $R_{36}$, $R_{37}$, $R_{38}$, and m are as previously defined.

In certain embodiments, the compound of Formula (I) is represented by one of Formulae (X-1) and (X-2):

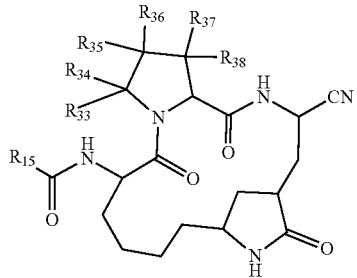

(X-1)

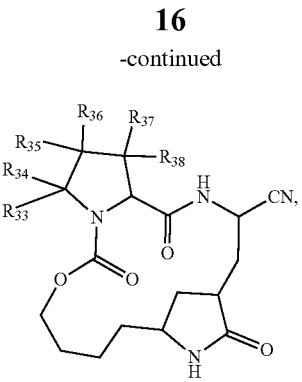

(X-2)

wherein $R_{15}$, $R_{33}$, $R_{34}$, $R_{35}$, $R_{36}$, $R_{37}$, and $R_{38}$ are as previously defined.

In certain embodiments, the compound of Formula (I) is represented by one of Formulae (X-1a) and (X-2a):

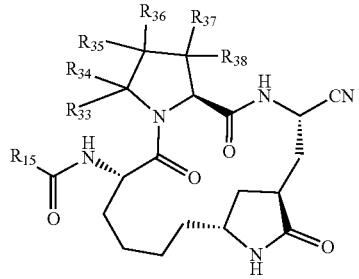

(X-1a)

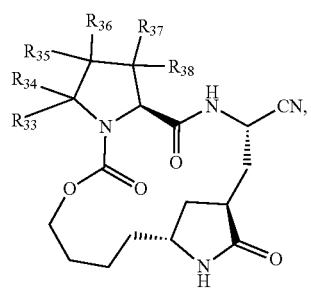

(X-2a)

wherein $R_{15}$, $R_{33}$, $R_{34}$, $R_{35}$, $R_{36}$, $R_{37}$, and $R_{38}$ are as previously defined.

In certain embodiments, the compound of Formula (I) is represented by one of Formulae (XI-1)~(XI-6):

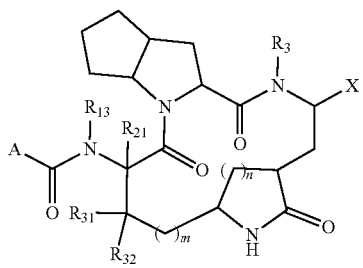

(XI-1)

-continued

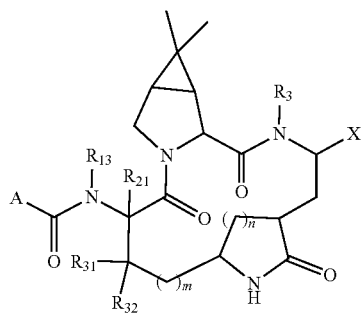
(XI-2)

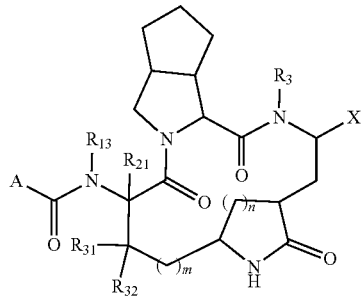
(XI-3)

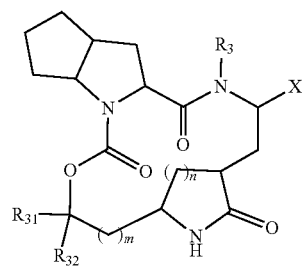
(XI-4)

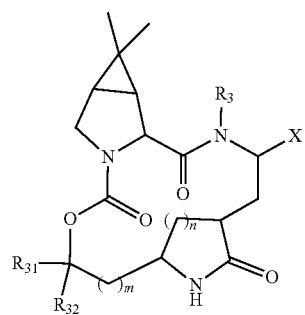
(XI-5)

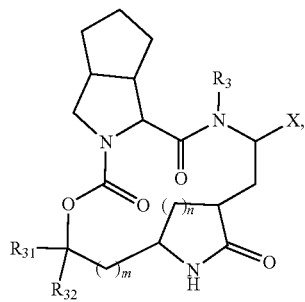
(XI-6)

wherein X, A, $R_3$, $R_{13}$, $R_{21}$, $R_{31}$, $R_{32}$, m, and n are as previously defined.

In certain embodiments, the compound of Formula (I) is represented by one of Formulae (XI-1)~(XI-2), wherein $R_{13}$ is hydrogen; R is hydrogen; n is 1; $R_3$ is hydrogen, -Me, —$CF_3$, or cyclopropyl; and X is selected from the following:

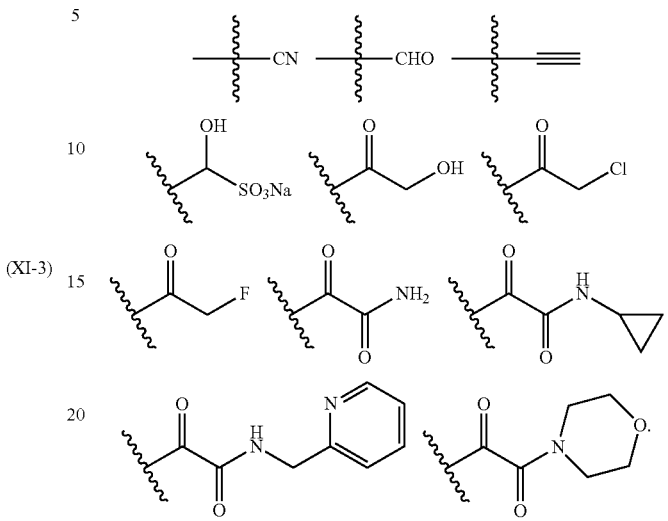

In certain embodiments, the compound of Formula (I) is represented by one of Formulae (XII-1)~(XII-6):

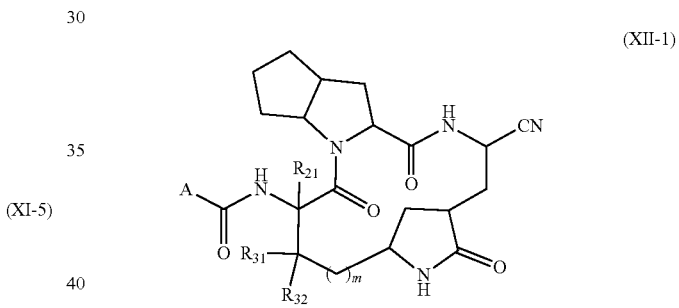
(XII-1)

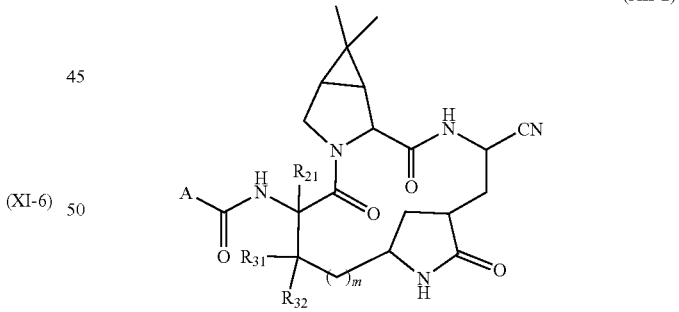
(XII-2)

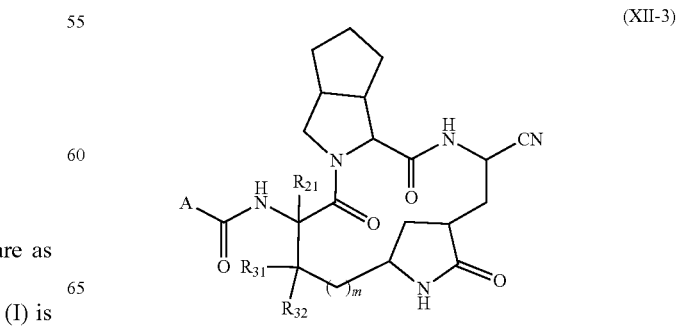
(XII-3)

-continued
(XII-4)
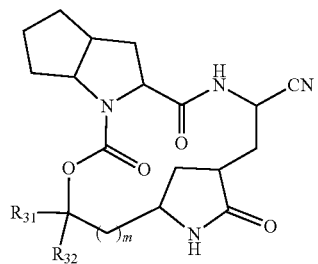
(XII-5)
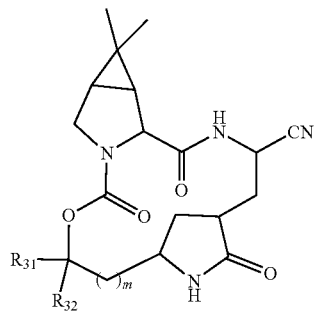
(XII-6)
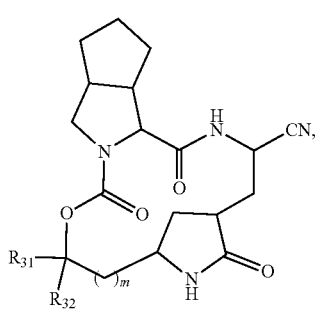
wherein A, $R_{31}$, $R_{32}$, and m are as previously defined.
In certain embodiments, the compound of Formula (I) is represented by one of Formulae (XII-1a)~(XII-6a):
(XII-1a)
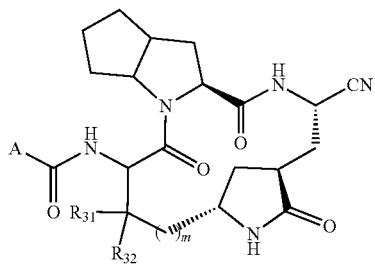
(XII-2a)
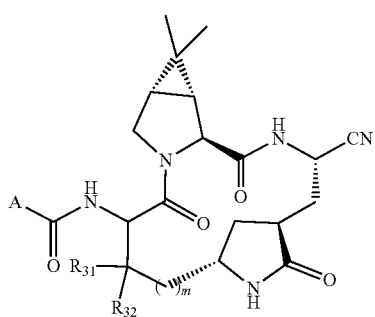
(XII-3a)
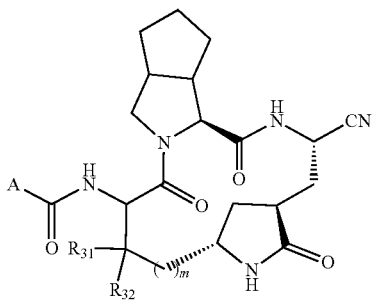
(XII-4a)
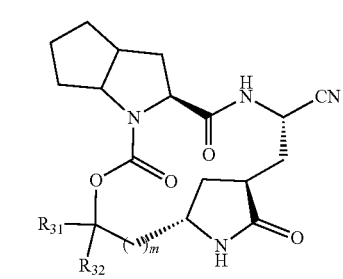
(XII-5a)
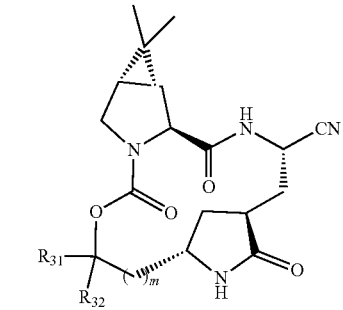
(XII-6a)
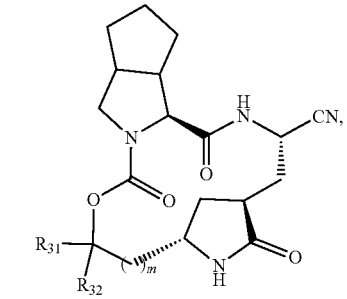
wherein A, $R_{31}$, $R_{32}$, and m are as previously defined.
In certain embodiments, the compound of Formula (I) is represented by Formula (XIII),
(XIII)
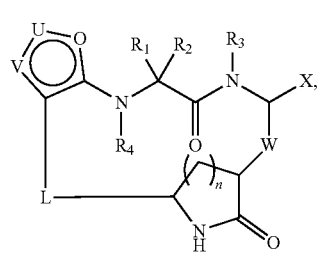

wherein V is nitrogen or —CR$_{16}$—; U is —CR$_{16}$—; R$_{16}$, n, W, X, L, R$_1$, R$_2$, R$_3$, and R$_4$ are as previously defined. Alternatively, U and V are both CR$_{16}$ and the two R$_{16}$ groups, together with the carbon atoms to which they are attached, form a fused carbocyclic or heterocyclic ring.

In certain embodiments, the compound of Formula (I) is represented by one of Formulae (XIV-1) and (XIV-2),

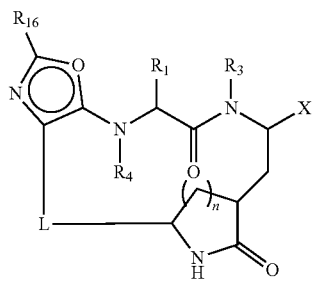

(XIV-1)

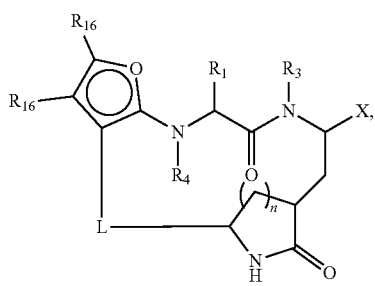

(XIV-2)

wherein n, X, L, R$_1$, R$_3$, R$_4$, and R$_{16}$ are as previously defined.

In certain embodiments, the compound of Formula (I) is represented by one of Formula (XV-1) and (XV-2),

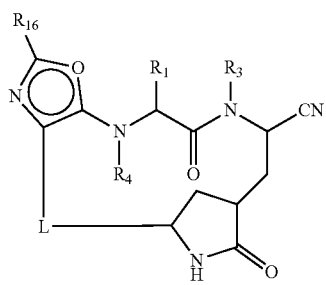

(XV-1)

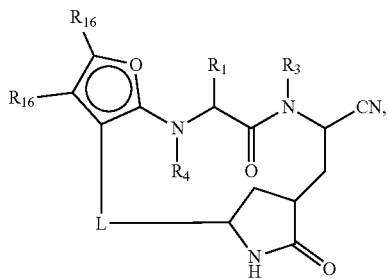

(XV-2)

wherein L, R$_1$, R$_3$, R$_4$, and R$_{16}$ are as previously defined.

In certain embodiments, the compound of Formula (I) is represented by Formula (XVI),

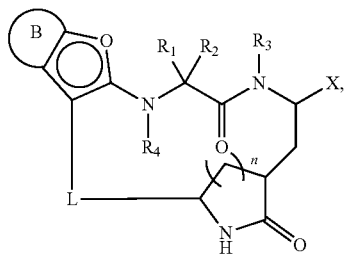

(XVI)

wherein B is optionally substituted —C$_3$-C$_8$ cycloalkenyl, optionally substituted 3- to 8-membered heterocycloalkenyl, optionally substituted aryl, optionally substituted heteroaryl; n, W, X, L, R$_1$, R$_2$, R$_3$, and R$_4$ are as previously defined.

In certain embodiments, the compound of Formula (I) is represented by Formula (XVII),

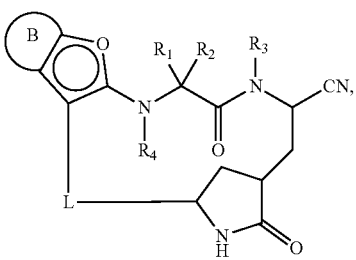

(XVII)

wherein B, L, R$_1$, R$_2$, R$_3$, and R$_4$ are as previously defined.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 2-methyl-2-buten-2-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 2-propynyl, 2-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond.

Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-2-enyl, bicyclo[4.2.1]non-3-en-12-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted. Preferably, as used herein, arylalkyl is aryl-$C_1$-$C_6$ alkyl, and heteroarylalkyl is heteroaryl-$C_1$-$C_6$ alkyl.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 2-propoxy, 2-propoxy (isopropoxy) and the higher homologs and isomers. Preferred alkoxy are ($C_2$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), S(O)$_2$, C(O)O, C(O)NH, OC(O)O, OC(O)NH, OC(O)$NH_2$, S(O)$_2$NH, S(O)$_2$$NH_2$, NHC(O)$NH_2$, NHC(O)C(O)NH, NHS(O)$_2$NH, NHS(O)$_2$$NH_2$, C(O)NHS(O)$_2$, C(O)NHS(O)$_2$NH or C(O)NHS(O)$_2$$NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 2-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —NO$_2$, —N$_3$, —CN, —NH$_2$, protected amino, oxo, thioxo, —NH—C$_1$-C$_{12}$-alkyl, —NH—C$_2$-C$_8$-alkenyl, —NH—C$_2$-C$_8$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_8$-alkenyl, —O—C$_2$-C$_8$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_8$-alkenyl, —C(O)—C$_2$-C$_8$-alkynyl, —C(O)—C$_3$-C$_{12}$-cycloalkyl, —C(O)-aryl, —C(O)— heteroaryl, —C(O)-heterocycloalkyl, —CONH$_2$, —CONH—C$_1$-C$_{12}$-alkyl, —CONH—C$_2$-C$_8$-alkenyl, —CONH—C$_2$-C$_8$-alkynyl, —CONH—C$_3$-C$_{12}$-cycloalkyl, —CONH-aryl, —CONH-heteroaryl, —CONH— heterocycloalkyl, —OCO$_2$—C$_1$-C$_{12}$-alkyl, —OCO$_2$—C$_2$-C$_8$-alkenyl, —OCO$_2$—C$_2$-C$_8$-alkynyl, —OCO$_2$—C$_3$-C$_{12}$-cycloalkyl, —OCO$_2$-aryl, —OCO$_2$-heteroaryl, —OCO$_2$-heterocycloalkyl, —CO$_2$—C$_1$-C$_{12}$ alkyl, —CO$_2$—C$_2$-C$_5$ alkenyl, —CO$_2$—C$_2$-C$_8$ alkynyl, CO$_2$—C$_3$-C$_{12}$-cycloalkyl, —CO$_2$— aryl, CO$_2$-heteroaryl, CO$_2$-heterocyloalkyl, —OCONH$_2$, —OCONH—C$_1$C$_{12}$-alkyl, —OCONH—C$_2$-C$_8$-alkenyl, —OCONH—C$_2$—C$_8$-alkynyl, —OCONH—C$_3$-C$_{12}$-cycloalkyl, —OCONH-aryl, —OCONH-heteroaryl, —OCONH-heterocyclo-alkyl, —NHC(O)H, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)-heterocyclo-alkyl, —NHCO$_2$—C$_1$-C$_{12}$-alkyl, —NHCO$_2$—C$_2$-C$_8$-alkenyl, —NHCO$_2$—C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$— heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl, —SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH— heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S-heterocycloalkyl, or methylthio-methyl. In certain embodiments, the substituents are independently selected from halo, preferably Cl and F; C$_1$-C$_4$-alkyl, preferably methyl and ethyl; halo-C$_1$-C$_4$-alkyl, such as fluoromethyl, difluoromethyl, and trifluoromethyl; C$_2$-C$_4$-alkenyl; halo-C$_2$-C$_4$-alkenyl; C$_3$-C$_6$-cycloalkyl, such as cyclopropyl; C$_1$-C$_4$-alkoxy, such as methoxy and ethoxy; halo-C$_1$-C$_4$-alkoxy, such as fluoromethoxy, difluoromethoxy, and trifluoromethoxy; acetyl; —CN; —OH; NH$_2$; C$_1$-C$_4$-alkylamino; di(C$_1$-C$_4$-alkyl) amino; and NO$_2$. It is understood that the aryls, heteroaryls, alkyls, and the like can be further substituted. In some cases, each substituent in a substituted moiety is additionally optionally substituted with one or more groups, each group being independently selected from C$_1$-C$_4$-alkyl; —CF$_3$, —OCH$_3$, —OCF$_3$, —F, —Cl, —Br, —I, —OH, —NO$_2$, —CN, and —NH$_2$. Preferably, a substituted alkyl group is substituted with one or more halogen atoms, more preferably one or more fluorine or chlorine atoms.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs. Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 12-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*. John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, $2^{nd}$ d Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds, and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 2-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Antiviral Activity

In certain embodiments, the present invention provides a method of treating or preventing a viral infection in a subject in need thereof, comprising administering to the subject a therapeutically effective amount of a compound of Formula (I) or a pharmaceutically acceptable salt thereof. The viral infection is preferably a coronavirus infection. In certain embodiments, the coronavirus is SARS-CoV-1, SARS-CoV-2, or MERS-CoV. Preferably the coronavirus is SARS-CoV-2.

A viral inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). A therapeutically effective amount of the compound described above may range, for example, from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Combination and Alternation Therapy

The compounds of the present invention may be used in combination with one or more antiviral therapeutic agents or anti-inflammatory agents useful in the prevention or treatment of viral diseases or associated pathophysiology. Thus, the compounds of the present invention and their salts, solvates, or other pharmaceutically acceptable derivatives thereof, may be employed alone or in combination with other antiviral or anti-inflammatory therapeutic agents. The compounds herein and pharmaceutically acceptable salts thereof may be used in combination with one or more other agents which may be useful in the prevention or treatment of respiratory disease, inflammatory disease, autoimmune disease, for example; anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast, pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-ethylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-lgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents), suitable anti-infective agents including antibiotic agents, antifungal agents, antheimintic agents, antimalarial agents, antiprotozoal agents, antituberculosis agents, and antiviral agents, including those listed at https://www.drugs.com/drug-class/anti-infectives.html. In general, combination therapy is typically preferred over alternation therapy because it induces multiple simultaneous stresses on the virus.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The "additional therapeutic or prophylactic agents" include but are not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or anti-microbial and anti-viral agents (e.g. ribavirin and amantidine). The compositions according to the invention may also be used in combination with gene replacement therapy.

ABBREVIATIONS

Abbreviations which may be used in the descriptions of the scheme and the examples that follow are: Ac for acetyl; AcOH for acetic acid; Boc$_2$O for di-tert-butyl-dicarbonate; Boc for t-butoxycarbonyl; Bz for benzoyl; Bn for benzyl; t-BuOK for potassium tert-butoxide; Brine for sodium chloride solution in water; CDI for carbonyldiimidazole; DCM or CH$_2$Cl$_2$ for dichloromethane; CH$_3$ for methyl; CH$_3$CN for acetonitrile; (COCl)$_2$ for oxalyl chloride; Cl$_2$CHCN for dichloroacetonitrile; Cs$_2$CO$_3$ for cesium carbonate; CuCl for copper (I) chloride; CuI for copper (I) iodide; CuSO$_4$ for copper (II) sulfate; dba for dibenzylidene acetone; DBU for 1,8-diazabicyclo[5.4.0]-undec-7-ene; DIBAL-H for diisobutylaluminum hydride; DIPEA or (i-Pr)$_2$EtN for N,N,-diisopropylethyl amine; DMP or Dess-Martin periodinane for 1,1,2-tris(acetyloxy)-1,2-dihydro-1,2-benziodoxol-3-(1H)-one; DMAP for 4-dimethylamino-pyridine; DME for 1,2-dimethoxyethane; DMF for N,N-dimethylformamide; DMSO for dimethyl sulfoxide; EDC for 1-ethyl-3-(3-dimethylaminopropyl)carbodiimide; EtOAc for ethyl acetate; EtOH for ethanol; Et$_2$O for diethyl ether; H$_2$ for hydrogen, HATU for O-(7-azabenzotriazol-2-yl)-N,N,N',N',-tetramethyluronium Hexafluoro-phosphate; HCl for hydrogen chloride; K$_2$CO$_3$ for potassium carbonate; n-BuLi for n-butyl lithium; KHMDS for potassium bis(trimethylsilyl)amide; IBX for 2-iodoxybenzoic acid; In for indium; LDA for lithium diisopropylamide; Li for lithium; LiBH$_4$ for lithium borohydride; LiBr for lithium bromide; LiHMDS for lithium bis(trimethylsilyl)amide; LiOH for lithium hydroxide; LiTMP for lithium 2,2,6,6-tetramethyl-piperidinate; MeOH for methanol; Mg for magnesium; MOM for methoxymethyl; Ms for mesyl or —SO$_2$—CH$_3$; NaHMDS for sodium bis(trimethylsilyl)amide; NaCl for sodium chloride; NaH for sodium hydride; NaHCO$_3$ for sodium bicarbonate or sodium hydrogen carbonate; Na$_2$CO$_3$ sodium carbonate; NaOH for sodium hydroxide; Na$_2$SO$_4$ for sodium sulfate; NaHSO$_3$ for sodium bisulfite or sodium hydrogen sulfite; Na$_2$S$_2$O$_3$ for sodium thiosulfate; NH$_3$ for ammonia; NH$_4$OH for ammonium hydroxide; NH$_2$NH$_2$ for hydrazine; NH$_4$Cl for ammonium chloride; Ni for nickel; NMM for N-methylmorpholine; OH for hydroxyl; OsO$_4$ for osmium tetroxide; OTf for triflate; PPA for polyphophoric acid; PTSA for p-toluenesulfonic acid; PPTS for pyridinium p-toluenesulfonate; SO$_3$ for sulfur trioxide; TBAF for tetrabutylammonium fluoride; TEA or Et$_3$N for triethylamine; TFA for trifluoroacetic acid; TFAA for trifluoroacetic anhydride; THF for tetrahydrofuran; T$_3$P for propylphosphonic anhydride; TPP or PPh$_3$ for triphenyl-phosphine; Tos or Ts for tosyl or —SO$_2$—C$_6$H$_4$CH$_3$; Ts$_2$O for tolylsulfonic anhydride or tosyl-anhydride; TsOH for p-tolylsulfonic acid; Pd for palladium; Pd/C for palladium on carbon; Ph for phenyl; Pd$_2$(dba)$_3$ for tris(diben-zylideneacetone) dipalladium (0); Pd(PPh$_3$)$_4$ for tetrakis(triphenylphosphine)-palladium (0); PdCl$_2$(PPh$_3$)$_2$ for trans-dichlorobis-(triphenylphosphine) palladium (II); Pd(TFA)$_2$ for palladium(II) trifluoroacetate; for Pt for platinum; Rh for rhodium; rt for room temperature; Ru for ruthenium; TBS for tert-butyl dimethylsilyl; TMS for trimethylsilyl; or TMSCl for trimethylsilyl chloride; Zhan 1B cat. for dichloro[1,3-bis(2,4,6-trimethylphenyl)-2-imidazolidinylidene][[5-[(dimethylamino)sulfonyl]-2-(1-methylethoxy-O)phenyl]methylene-C]ruthenium(II).

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

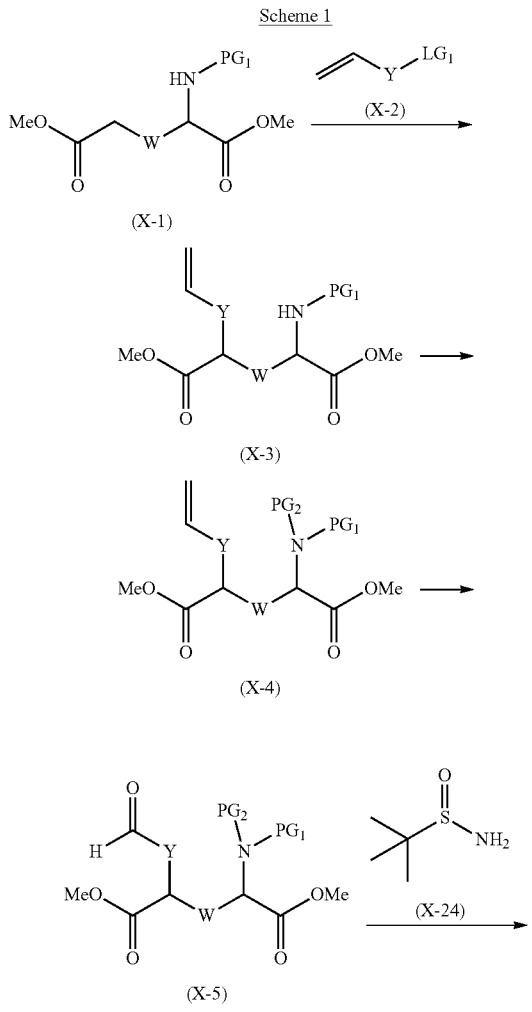

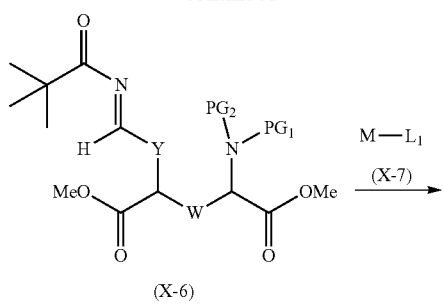
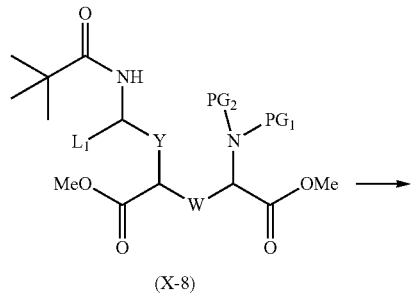
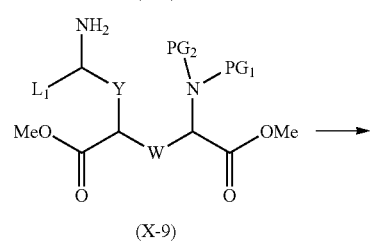
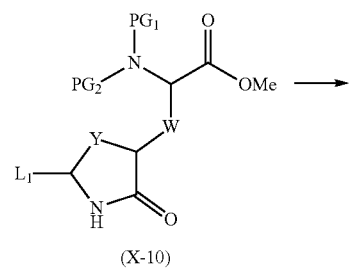
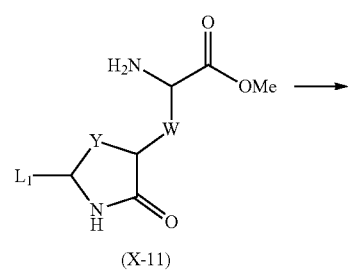
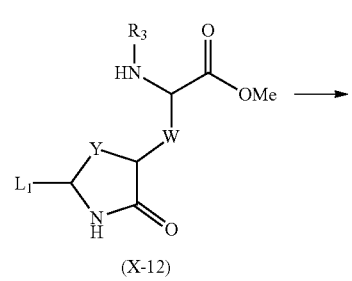
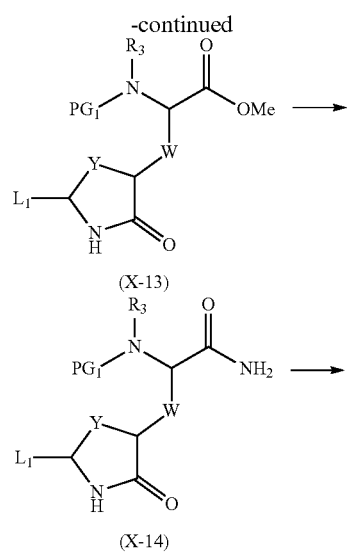
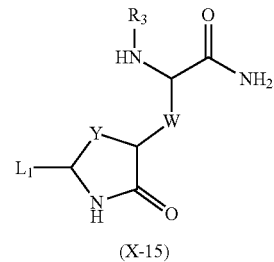
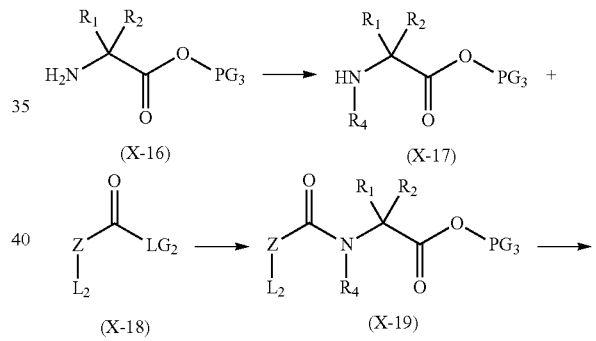
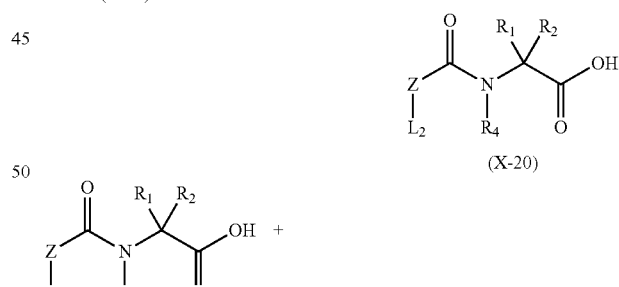
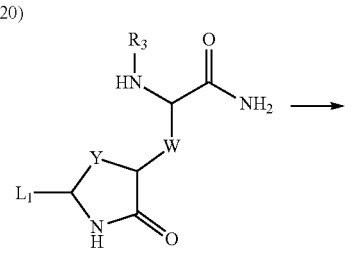

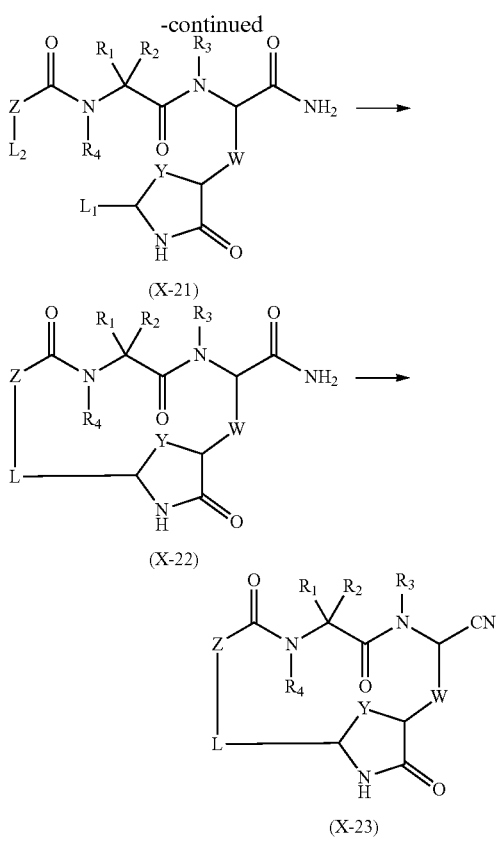

Scheme 1 illustrates a general method to prepare the nitrile compound (X-23) of formulae (I) from the amino ester compound (X-1), wherein W is as previously defined and $PG_1$ is an appropriate protecting group (e.g. Boc, Cbz or Fmoc), and alkene (X-2), wherein Y is previously defined and $LG_1$ is an appropriate leaving group (e.g. Br, I, OMs, or OTs). α-Deprotonation of ester (X-1) with strong base (e.g. LDA, LiTMP, LiHMDS, NaHMDS, or KHMDS) affords the resulting enolate, which is further reacted with alkene (X-2) to provide the α-substituted ester (X-3). Introduction of another protecting group $PG_2$ (e.g. Boc, Cbz or Fmoc) to carbamate (X-3) generates the alkene (X-4), whose olefin is converted to the aldehyde (X-5) by ozonlysis-Criegee reaction or Lemieux-Johnson oxidation. Condensation of the aldehyde (X-5) with Ellman's tert-butanesulfinamide (X-24) affords the aldimine (X-6). Nucleophilic addition of the aldimine (X-6) with the organometallic reagent (X-7), wherein M is the corresponding metal component (e.g. Li, MgBr, ZnBr or InBr, etc.) and Li is the corresponding functionality to form the macrocycle linkage L that is as previously defined, provides the chiral sulfinamide (X-8). On addition of HCl, the tert-butanesulfinyl group is removed to give the chiral amine (X-9), which was further treated under basic conditions (e.g. DIPEA) to form the lactam (X-10). $PG_1$ and $PG_2$ are both removed using the corresponding conditions (e.g. TFA, HCl, etc.) to afford the amine (X-11). $R_3$, as previously defined, is introduced through a reductive amination to provide the amine (X-12), which is protected with $PG_1$ to form the ester (X-13). If $R_3$ is hydrogen, the selective $PG_2$ removal (e.g. LiBr) from the compound (X-10) directly affords the ester (X-13). Treatment of ester (X-13) with $NH_3$ (e. g. ammonia in MeOH, $NH_4OH$, etc.) affords the primary amide (X-14), which was converted to the key amine component (X-15) by removal of protecting group $PG_1$ using the appropriate conditions (e.g. TFA, HCl, etc).

The synthesis of the other component starts from the reductive amination of the amino ester (X-16), wherein $R_1$ and $R_2$ are previously defined and $PG_3$ is $C_1$-$C_4$ alkyl, to introduce $R_4$, as previously defined, to the amine (X-17). Coupling of the amine (X-17) with the compound (X-18), wherein Z is as previously defined and $LG_2$ is the leaving group (e.g. Cl, OAt, OBt, e.g.) and L2 is the other corresponding functionality to form the macrocycle linkage L that is as previously defined, affords the amino ester (X-19). $PG_3$ is removed under basic conditions (e.g. LiOH) to provide the amino acid component (X-20).

The amide coupling of the amino acid (X-20) with the amine (X-15) using appropriate amide coupling reagents (e.g. HATU, EDC, etc.) affords the linear peptide (X-21). Macrocyclization of the linear peptide (X-21) through well-known cyclization approaches (e.g. ring closing metathesis, intramolecular click chemistry, intramolecular Suzuki coupling, macrolactamization, intramolecular Mitsunobu reaction, intramolecular $S_NAr$, intramolecular alkylation, etc.) ties up Li and L2 together to form macrocyclic compound (X-22), wherein L is as previously defined. These widely-used macrocyclicaton approaches have been reviewed in the literature (Marsault, E. et al. "Macrocycles Are Great Cycles: Applications, Opportunities, and Challenges of Synthetic Macrocycles in Drug Discovery" J. Med. Chem. 2011, 54, 7, 1961-2004). For example, the application of ring closing metathesis in synthesis of macrocyclic compounds has been reported in the literature (Yu, M. et al. "Ring-Closing Metathesis in Pharmaceutical Development: Fundamentals, Applications, and Future Directions" Org. Process Res. Dev. 2018, 22, 8, 918-946; Damalanka, V. C. et al. "Design, synthesis, and evaluation of a novel series of macrocyclic inhibitors of norovirus 3CL protease" European Journal of Medicinal Chemistry, Volume 127, 15 Feb. 2017, Pages 41-61). The application of intramolecular Suzuki coupling in synthesis of macrocyclic compounds has been reported in the literature (Li, H. et al. "Synthesis of Bis-Macrocyclic HCV Protease Inhibitor MK-6325 via Intramolecular $sp^2$-$sp^3$ Suzuki-Miyaura Coupling and Ring Closing Metathesis" Org. Lett. 2015, 17, 6, 1533-1536). The application of intramolecular click chemistry in synthesis of macrocyclic compounds has been reported in the literature (Weerawarna, P. M. et al. "Structure-based design and synthesis of triazole-based macrocyclic inhibitors of norovirus protease: Structural, biochemical, spectroscopic, and antiviral studies" European Journal of Medicinal Chemistry, Volume 119, 25 Aug. 2016, Pages 300-318). The application of macrolactamization in synthesis of macrocyclic compounds has been reported in the literature (Li, B. et al. "Exploratory Process Development of Lorlatinib" Org. Process Res. Dev. 2018, 22, 1289-1293). The macrocyclization approaches that forms L are not limited to these mentioned above. The amide (X-22) is converted to the nitrile compound (X-23) under dehydration conditions (e.g. TFAA/$Et_3N$, $Pd(TFA)_2/Cl_2CHCN$ or $T_3P$).

Scheme 2

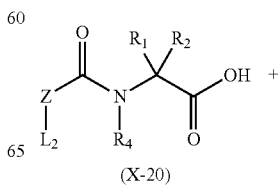

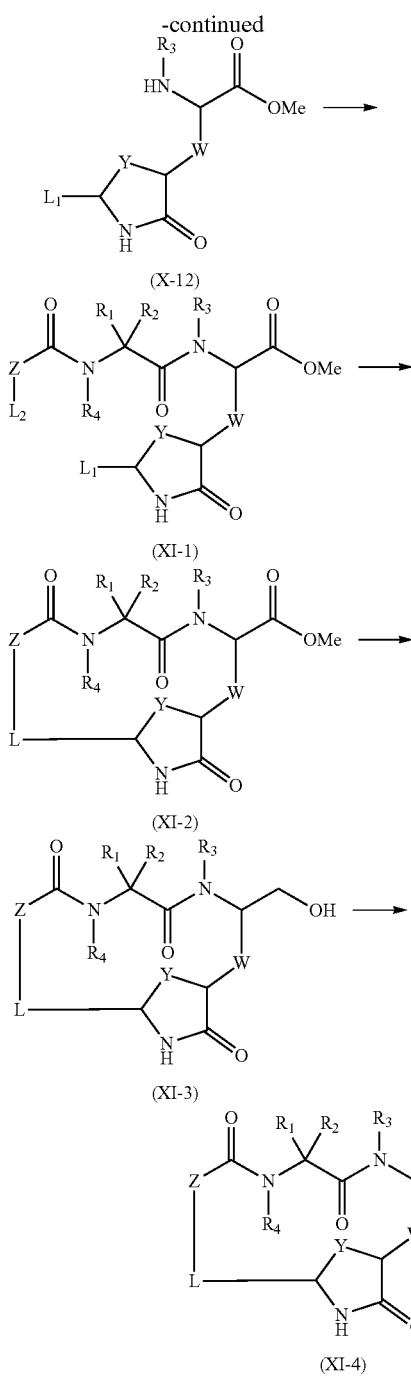

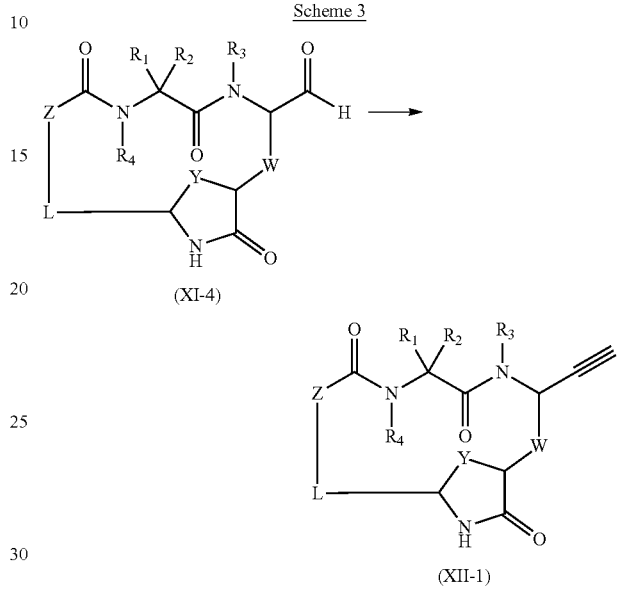

Scheme 2 illustrates a general method to synthesize the aldehyde compound (XI-4) of formula (I). The amide coupling of the amino acid (X-20), wherein $R_1$, $R_2$, $R_4$, Z and L2 are as previously defined, with the amine (X-12), wherein $R_3$, W, Y and $L_1$ are as previously defined, using appropriate amide coupling reagents (e.g. HATU, EDC, etc.) affords the linear peptide (XI-1). Macrocyclization of the linear peptide (XI-1) through well-known cyclization approaches (e.g. ring closing metathesis, intramolecular click chemistry, intramolecular Suzuki coupling, macrolactamization, intramolecular Mitsunobu reaction, intramolecular $S_NAr$, intramolecular alkylation, etc.) ties up Li and L2 together to form macrocyclic compound (XI-2), wherein L is as previously defined. The macrocyclization approaches that forms L are not limited to these mentioned above. The ester (XI-2) is reduced to the alcohol (XI-3) by employing reducing reagents (e.g. LiBH$_4$, or DIBAL-H). Oxidation of the alcohol (XI-3) with mild oxidation reagents (e.g. Dess-Martin periodinane, IBX, SO$_3$-pyridine/DMSO/Et$_3$N) produces the aldehyde compound (XI-4).

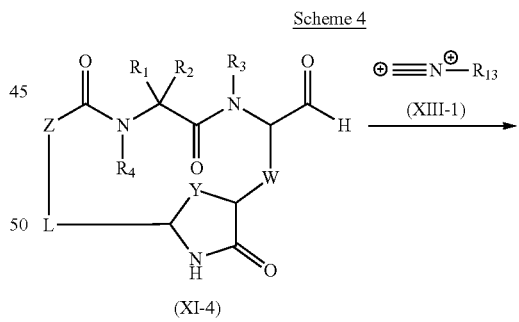

Scheme 3 illustrates a general method to synthesize the alkyne compound (XII-1) of formula (I). The alkyne compound (XII-1) is prepared by Seyferth-Gilbert homologation or Corey-Fuchs reaction from the aldehyde compound (XI-4), wherein $R_1$, $R_2$, $R_3$, $R_4$, W, Y, Z, and L are as previously defined.

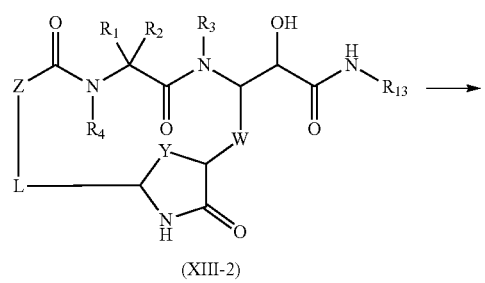

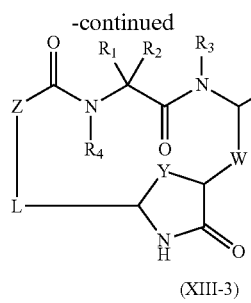

(XIII-3)

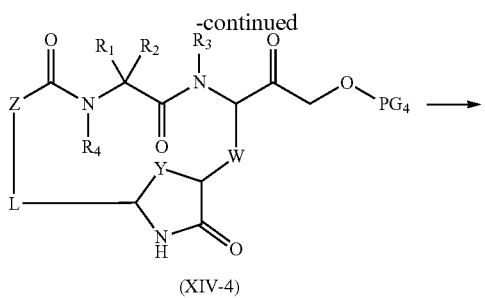

(XIV-4)

Scheme 4 illustrates a general method to synthesize the α-ketoamide compound (XIII-3) of formula (I). Treatment of the aldehyde (XI-4), wherein $R_1$, $R_2$, $R_3$, $R_4$, W, Y, Z, and L are as previously defined, with isonitrile compound (XIII-1), wherein $R_{13}$ is previously defined, affords the α-hydroxylamide (XIII-2). Oxidation of the alcohol (XIII-2) with appropriate oxidants (e.g. Dess-Martin periodinane, $(COCl)_2$/DMSO/$Et_3N$, PCC, or $SO_3$-pyridine/DMSO/$Et_3N$) affords α-ketoamide compound (XIII-3).

Scheme 5

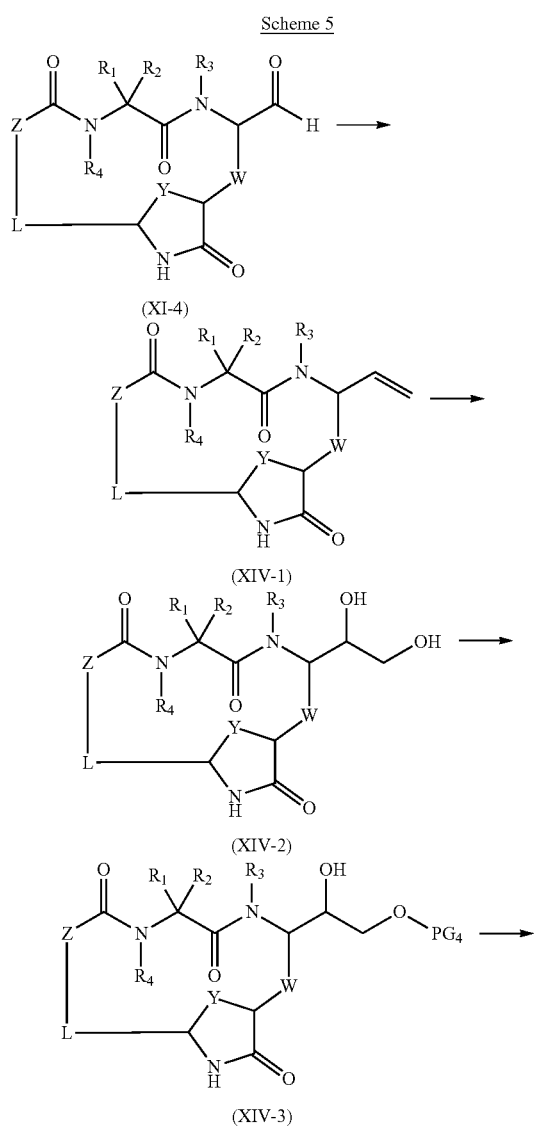

Scheme 5 illustrates a general method to synthesize the hydroxyketone compound (XIV-5) of formula (I). The Wittig reaction of the aldehyde (XI-4), wherein $R_1$, $R_2$, $R_3$, $R_4$, W, Y, Z, and L are as previously defined, provides the alkene (XIV-1). Dihydroxylation of the alkene (XIV-1) affords the diol (XIV-2), whose primary alcohol is selectively protected with an appropriate protecting group $PG_4$ (e.g. TBS) to form the alcohol (XIV-3). Oxidation of the alcohol (XIV-3) with appropriate oxidants (e.g. Dess-Martin periodinane, $(COCl)_2$/DMSO/$Et_3N$, PCC, or $SO_3$-pyridine/DMSO/$Et_3N$) affords the ketone (XIV-4). The removal of $PG_4$ using appropriate conditions (e.g. TBAF) provides the hydroxyketone compound (XIV-5).

EXAMPLES

The compounds and processes of the present invention will be better understood in connection with the following examples, which are intended as an illustration only and not limiting of the scope of the invention. Starting materials were either available from a commercial vendor or produced by methods well known to those skilled in the art.

General Conditions:

Mass spectra were run on LC-MS systems using electrospray ionization. These were Agilent 1290 Infinity II systems with an Agilent 6120 Quadrupole detector. Spectra were obtained using a ZORBAX Eclipse XDB-C18 column (4.6×30 mm, 1.8 micron). Spectra were obtained at 298K using a mobile phase of 0.1% formic acid in water (A) and 0.1% formic acid in acetonitrile (B). Spectra were obtained with the following solvent gradient: 5% (B) from 0-1.5 min, 5-95% (B) from 1.5-4.5 min, and 95% (B) from 4.5-6 min. The solvent flowrate was 1.2 mL/min. Compounds were detected at 210 nm and 254 nm wavelengths. $[M+H]^+$ refers to mono-isotopic molecular weights.

NMR spectra were run on a Bruker 400 MHz spectrometer. Spectra were measured at 298K and referenced using the solvent peak. Chemical shifts for $^1H$ NMR are reported in parts per million (ppm).

Compounds were purified via reverse-phase high-performance liquid chromatography (RPHPLC) using a Gilson GX-281 automated liquid handling system. Compounds were purified on a Phenomenex Kinetex EVO C18 column (250×21.2 mm, 5 micron), unless otherwise specified. Compounds were purified at 298K using a mobile phase of water (A) and acetonitrile (B) using gradient elution between 0% and 100% (B), unless otherwise specified. The solvent flowrate was 20 mL/min and compounds were detected at 254 nm wavelength.

Alternatively, compounds were purified via normal-phase liquid chromatography (NPLC) using a Teledyne ISCO Combiflash purification system. Compounds were purified on a REDISEP silica gel cartridge. Compounds were purified at 298K and detected at 254 nm wavelength.

Example 1

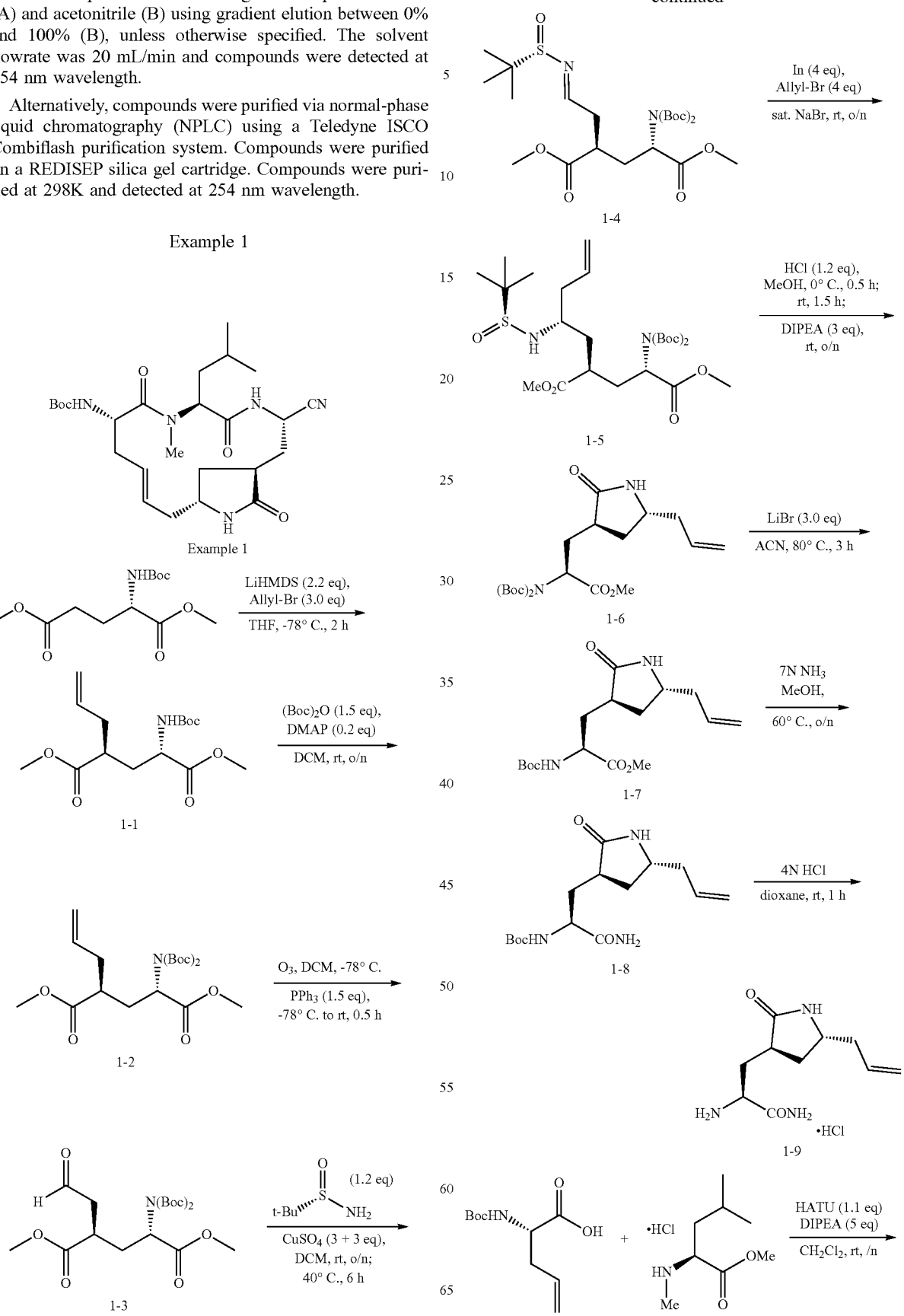

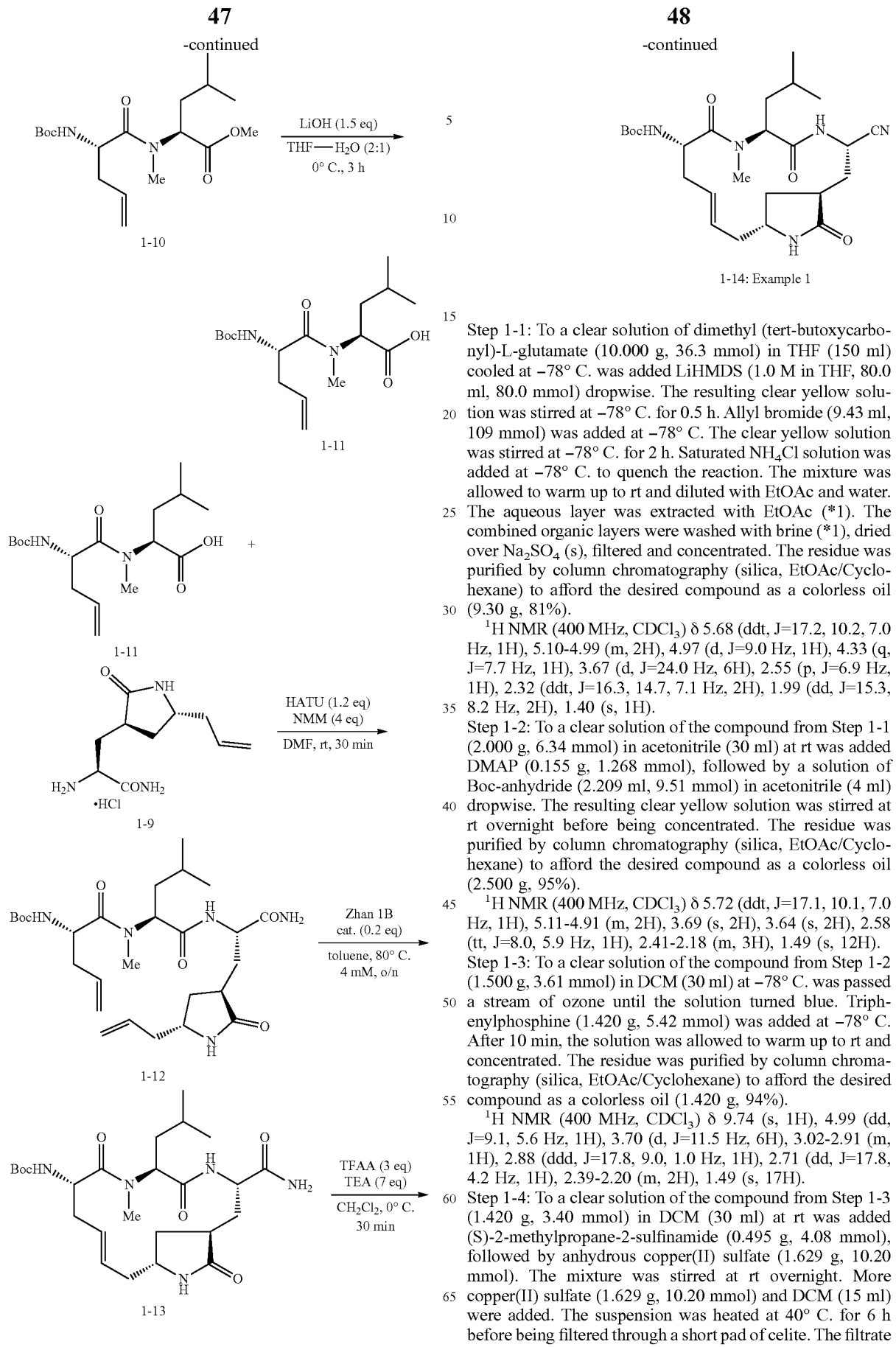

Step 1-1: To a clear solution of dimethyl (tert-butoxycarbonyl)-L-glutamate (10.000 g, 36.3 mmol) in THF (150 ml) cooled at −78° C. was added LiHMDS (1.0 M in THF, 80.0 ml, 80.0 mmol) dropwise. The resulting clear yellow solution was stirred at −78° C. for 0.5 h. Allyl bromide (9.43 ml, 109 mmol) was added at −78° C. The clear yellow solution was stirred at −78° C. for 2 h. Saturated NH$_4$Cl solution was added at −78° C. to quench the reaction. The mixture was allowed to warm up to rt and diluted with EtOAc and water. The aqueous layer was extracted with EtOAc (*1). The combined organic layers were washed with brine (*1), dried over Na$_2$SO$_4$ (s), filtered and concentrated. The residue was purified by column chromatography (silica, EtOAc/Cyclohexane) to afford the desired compound as a colorless oil (9.30 g, 81%).

$^1$H NMR (400 MHz, CDCl$_3$) δ 5.68 (ddt, J=17.2, 10.2, 7.0 Hz, 1H), 5.10-4.99 (m, 2H), 4.97 (d, J=9.0 Hz, 1H), 4.33 (q, J=7.7 Hz, 1H), 3.67 (d, J=24.0 Hz, 6H), 2.55 (p, J=6.9 Hz, 1H), 2.32 (ddt, J=16.3, 14.7, 7.1 Hz, 2H), 1.99 (dd, J=15.3, 8.2 Hz, 2H), 1.40 (s, 1H).

Step 1-2: To a clear solution of the compound from Step 1-1 (2.000 g, 6.34 mmol) in acetonitrile (30 ml) at rt was added DMAP (0.155 g, 1.268 mmol), followed by a solution of Boc-anhydride (2.209 ml, 9.51 mmol) in acetonitrile (4 ml) dropwise. The resulting clear yellow solution was stirred at rt overnight before being concentrated. The residue was purified by column chromatography (silica, EtOAc/Cyclohexane) to afford the desired compound as a colorless oil (2.500 g, 95%).

$^1$H NMR (400 MHz, CDCl$_3$) δ 5.72 (ddt, J=17.1, 10.1, 7.0 Hz, 1H), 5.11-4.91 (m, 2H), 3.69 (s, 2H), 3.64 (s, 2H), 2.58 (tt, J=8.0, 5.9 Hz, 1H), 2.41-2.18 (m, 3H), 1.49 (s, 12H).

Step 1-3: To a clear solution of the compound from Step 1-2 (1.500 g, 3.61 mmol) in DCM (30 ml) at −78° C. was passed a stream of ozone until the solution turned blue. Triphenylphosphine (1.420 g, 5.42 mmol) was added at −78° C. After 10 min, the solution was allowed to warm up to rt and concentrated. The residue was purified by column chromatography (silica, EtOAc/Cyclohexane) to afford the desired compound as a colorless oil (1.420 g, 94%).

$^1$H NMR (400 MHz, CDCl$_3$) δ 9.74 (s, 1H), 4.99 (dd, J=9.1, 5.6 Hz, 1H), 3.70 (d, J=11.5 Hz, 6H), 3.02-2.91 (m, 1H), 2.88 (ddd, J=17.8, 9.0, 1.0 Hz, 1H), 2.71 (dd, J=17.8, 4.2 Hz, 1H), 2.39-2.20 (m, 2H), 1.49 (s, 17H).

Step 1-4: To a clear solution of the compound from Step 1-3 (1.420 g, 3.40 mmol) in DCM (30 ml) at rt was added (S)-2-methylpropane-2-sulfinamide (0.495 g, 4.08 mmol), followed by anhydrous copper(II) sulfate (1.629 g, 10.20 mmol). The mixture was stirred at rt overnight. More copper(II) sulfate (1.629 g, 10.20 mmol) and DCM (15 ml) were added. The suspension was heated at 40° C. for 6 h before being filtered through a short pad of celite. The filtrate was concentrated. The residue was purified by column chromatography (silica, EtOAc/Cyclohexane) to afford the desired compound as a colorless sticky oil (1.400 g, 79%).

$^1$H NMR (400 MHz, CDCl$_3$) δ 8.03 (t, J=3.4 Hz, 1H), 5.00 (dd, J=8.1, 6.4 Hz, 1H), 3.68 (d, J=23.0 Hz, 6H), 2.97-2.84 (m, 2H), 2.83-2.71 (m, 1H), 2.40-2.27 (m, 2H), 1.49 (s, 18H), 1.16 (s, 9H). ESI MS m/z=543.21 [M+Na]$^+$.

Step 1-5: To a flask containing the compound from Step 1-4 (1.400 g, 2.69 mmol) and Indium (1.235 g, 10.76 mmol) at rt was added saturated NaBr solution (50 ml), followed by allyl bromide (0.931 ml, 10.76 mmol). The mixture was vigorously stirred at rt overnight. It turned into a white suspension. Saturated NaHCO$_3$ solution was added at rt to quench the reaction. The milky mixture was extracted with EtOAc (*2). The combined organic layers were washed with brine (*1), dried over Na$_2$SO$_4$ (s), filtered and concentrated. The residue was purified by column chromatography (silica, EtOAc/Cyclohexane) to afford the desired compound as a colorless oil (1.420 g, 94%).

$^1$H NMR (400 MHz, CDCl$_3$) δ 5.76 (dddd, J=20.8, 9.5, 8.0, 6.5 Hz, 1H), 5.19-5.10 (m, 2H), 4.93 (dd, J=8.0, 6.5 Hz, 1H), 3.68 (d, J=12.5 Hz, 7H), 3.21 (s, 2H), 2.77 (dtd, J=11.1, 7.0, 4.0 Hz, 1H), 2.53-2.42 (m, 1H), 2.39 (dt, J=13.8, 6.8 Hz, 1H), 2.32-2.16 (m, 2H), 1.86 (ddd, J=14.2, 10.6, 3.2 Hz, 1H), 1.68 (s, 1H), 1.58 (td, J=9.8, 4.9 Hz, 1H), 1.49 (s, 18H), 1.37 (d, J=26.4 Hz, 1H). ESI MS m/z=585.26 [M+Na]$^+$.

Step 1-6: To a solution of the compound from Step 1-5 (1.120 g, 1.990 mmol) in MeOH (11 ml) at 0° C. was added HCl (3 M in MeOH, 0.862 ml, 2.59 mmol). The solution was stirred at 0° C. for 0.5 h and then at rt for 1.5 h. DIPEA (1.043 ml, 5.97 mmol) was added at rt. The clear solution was stirred at rt overnight before being concentrated. The residue was purified by column chromatography (silica, EtOAc/Cyclohexane) to afford the desired compound as a colorless oil (0.750 g, 88%).

$^1$H NMR (400 MHz, CDCl$_3$) δ 5.82 (s, 1H), 5.72 (dddd, J=17.7, 9.1, 7.8, 6.4 Hz, 1H), 5.19-5.06 (m, 2H), 5.02 (dd, J=9.8, 4.5 Hz, 1H), 3.71 (s, 3H), 3.72-3.60 (m, 2H), 2.51-2.37 (m, 2H), 2.30-2.21 (m, 1H), 2.21-2.10 (m, 1H), 2.08 (ddd, J=15.3, 6.3, 3.3 Hz, 1H), 2.05-1.91 (m, 1H), 1.77 (s, 1H), 1.50 (s, 18H). ESI MS m/z=449.20 [M+Na]$^+$.

Step 1-7: To a solution of the compound from Step 1-6 (0.750 g, 1.758 mmol) in acetonitrile (20 ml) at rt was added lithium bromide (0.458 g, 5.28 mmol). The resulting cloudy solution was stirred at 80° C. for 3 h. The mixture was allowed to cool down to rt and concentrated. The residue was diluted with DCM and water. The aqueous layer was extracted with DCM (*2). The combined organic layers were dried over Na$_2$SO$_4$ (s), filtered and concentrated. The residue was purified by column chromatography (silica, EtOAc/Cyclohexane) to afford the desired compound as a colorless oil (0.410 g, 71%).

$^1$H NMR (400 MHz, CDCl$_3$) δ 6.57 (s, 1H), 5.72 (ddt, J=17.7, 9.5, 7.1 Hz, 1H), 5.51 (d, J=8.4 Hz, 1H), 5.14-5.05 (m, 2H), 4.29 (ddd, J=11.7, 8.4, 3.6 Hz, 1H), 3.71 (s, 3H), 3.64 (p, J=3.8, 3.1 Hz, 1H), 2.52 (qd, J=8.9, 4.3 Hz, 1H), 2.33-2.19 (m, 1H), 2.19 (t, J=5.4 Hz, 1H), 2.18-2.11 (m, 1H), 2.06 (td, J=10.8, 5.5 Hz, 1H), 1.97 (dt, J=13.1, 8.3 Hz, 1H), 1.79 (ddd, J=13.9, 10.0, 3.8 Hz, 1H), 1.42 (s, 9H). ESI MS m/z=349.15 [M+Na]$^+$.

Step 1-8: A solution of the compound from Step 1-7 (0.410 g, 1.256 mmol) in ammonia (7 M in MeOH, 10.77 ml, 75 mmol) in a sealed tube was stirred at 60° C. overnight. The mixture was allowed to cool down to rt and concentrated. The residue was dried under vacuum to afford the desired compound as a light yellow solid (0.382 g, 98%).

$^1$H NMR (400 MHz, CD$_3$OD) δ 5.70 (dddd, J=15.9, 10.2, 7.7, 6.4 Hz, 1H), 5.10-5.00 (m, 1H), 5.04-4.97 (m, 1H), 4.06-3.95 (m, 1H), 3.65-3.50 (m, 1H), 2.45 (s, 1H), 2.24-1.84 (m, 4H), 1.69-1.54 (m, 1H), 1.35 (d, J=2.5 Hz, 9H). ESI MS m/z=334.16 [M+Na]$^+$.

Step 1-9: To a 20 mL vial containing compound from Step 1-8 (0.330 g, 1.060 mmol) was added a 4 N solution of HCl (4 ml, 16.00 mmol) in dioxane. The reaction was stirred for 1 h and concentrated in vacuo to give the desired product as a yellowish solid (0.263 g, 100%). ESI MS m/z=212.13 [M+H]$^+$.

Step 1-10: A solution of (S)-2-((tert-butoxycarbonyl)amino)pent-4-enoic acid (2 g, 9.29 mmol) and methyl methyl-L-leucinate, hydrochloride (1.8 g, 9.20 mmol) CH$_2$Cl$_2$ (50 ml) was treated with DIPEA (8 ml, 45.8 mmol) and HATU (3.9 g, 10.26 mmol). The reaction was stirred at room temperature overnight. The reaction was quenched with a saturated solution of sodium bicarbonate. The aqueous layer was extracted with dichloromethane over 2 times. The combined organic layer was dried over sodium sulfate, filtered and concentrated in vacuo. The crude product was added to an 80 g silica gel column and eluted by ethyl acetate/cyclohexane from 0% to 100% to give the desired product (3.0 g, 8.42 mmol, 91% yield) as a colorless syrup.

$^1$H NMR (500 MHz, Chloroform-d) δ 5.79 (ddt, J=17.2, 10.1, 7.2 Hz, 1H), 5.39-5.23 (m, 2H), 5.19-5.09 (m, 2H), 4.67 (dt, J=8.7, 6.4 Hz, 1H), 3.70 (s, 3H), 2.99 (s, 3H), 2.56-2.47 (m, 1H), 2.35 (dtt, J=14.1, 7.0, 1.2 Hz, 1H), 2.17 (s, 2H), 1.77-1.66 (m, 2H), 1.59 (d, J=4.2 Hz, 3H), 1.42 (s, 11H), 1.00-0.87 (m, 7H). ESI MS m/z=578.95 [M+Na]$^+$.

Step 1-11: A solution of the compound from Step 1-10 (2.91 g, 8.16 mmol) in THF (20 ml) and Water (10 ml) was treated with LiOH (290 mg, 12.11 mmol) at 0° C. The reaction was stirred at 0° C. for 3 h. The reaction was quenched with 1 N HCl until pH value is 2-3. The aqueous layer was extracted with ethyl acetate over 3 times. The combined organic layer was dried over sodium sulfate, filtered, and concentrated in vacuo to give the desired product (2.73 g, 7.97 mmol, 98% yield) as a white solid.

$^1$H NMR (500 MHz, Chloroform-d) δ 5.77 (ddt, J=17.2, 10.1, 7.2 Hz, 1H), 5.46-5.22 (m, 2H), 5.22-5.04 (m, 2H), 4.68 (dt, J=8.5, 6.3 Hz, 1H). ESI MS m/z=340.98 [M−H]$^−$.

Step 1-12: A solution of the compound from Step 1-9 (263 mg, 1.062 mmol) and the compound from Step 1-11 (463 mg, 1.352 mmol) in DMF (4 ml) was treated with N-methylmorpholine (450 μl, 4.09 mmol) and HATU (488 mg, 1.283 mmol). The reaction was stirred at room temperature for 30 min. The reaction was diluted with ethyl acetate and quenched with a saturated solution of sodium bicarbonate. The organic layer was washed with water and brine over 3 times, dried over sodium sulfate, filtered, and concentrated in vacuo. The crude product was added to a 24 g silica gel column and eluted by acetone/dichloromethane from 0% to 100% to give the desired product (522 mg, 0.974 mmol, 92% yield) as a white solid. ESI MS m/z=534.08 [M−H]$^−$.

Step 1-13: A solution of the compound from Step 1-12 (510 mg, 0.952 mmol) in toluene (200 ml) was freezed to −78° C. and degassed in vacuo for 30 min. The solution was treated with a solution of Zhan 1B cat. (138 mg, 0.188 mmol) in toluene (30 ml) at −78° C. The mixture was degassed in vacuo for another 15 min. The mixture was slowly warmed to 80° C. and stirred overnight. The mixture was concentrated in vacuo, added to a 40 g silica gel column, and eluted by methanol/dichloromethane from 0% to 20 min to give the desired product (248 mg, 0.489 mmol, 51% yield) as a brownish solid.

$^1$H NMR (500 MHz, Methanol-d$_4$) δ 8.23 (d, J=9.0 Hz, 1H), 5.56 (ddt, J=12.1, 10.0, 2.4 Hz, 1H), 5.50-5.38 (m, 1H), 5.07 (dd, J=10.4, 5.3 Hz, 1H), 4.71 (dd, J=11.9, 3.3 Hz, 1H), 4.38 (ddd, J=12.7, 9.0, 3.6 Hz, 1H), 3.79-3.70 (m, 1H), 3.20 (s, 2H), 2.65-2.56 (m, 1H), 2.44-2.24 (m, 3H), 2.20-2.07 (m, 3H), 1.96-1.79 (m, 2H), 1.78-1.69 (m, 1H), 1.62 (ddd, J=13.7, 12.3, 3.7 Hz, 1H), 1.54 (s, 1H), 1.41 (s, 8H), 1.24 (s, 2H), 0.94 (d, J=6.5 Hz, 3H), 0.86 (d, J=6.3 Hz, 2H). ESI MS m/z=505.93 [M−H]$^-$.

Step 1-14: A solution of the compound from Step 1-13 (14 mg, 0.028 mmol) in CH$_2$Cl2 (0.2 ml) was treated with TEA (26.9 μl, 0.193 mmol) and TFAA (11.69 μl, 0.083 mmol) at 0° C. The reaction was stirred at 0° C. for 30 min. The reaction was quenched with a saturated solution of sodium bicarbonate. The mixture was stirred at room temperature for 30 min. The aqueous layer was extracted with dichloromethane over 3 times. The combined organic layer was dried over sodium sulfate, filtered, and concentrated in vacuo. The crude was added to a 4 g silica gel column and eluted by acetone/dichloromethane from 0% to 100% to give desired product Example 1 (10 mg, 0.020 mmol, 74% yield) as a white solid.

$^1$H NMR (400 MHz, Methanol-d$_4$) δ 5.53 (dd, J=14.1, 10.9 Hz, 1H), 5.47-5.34 (m, 1H), 5.00 (dd, J=9.9, 5.8 Hz, 1H), 4.69 (dd, J=11.8, 3.3 Hz, 1H), 4.58 (s, 1H), 3.74 (d, J=9.1 Hz, 1H), 3.21 (d, J=4.3 Hz, 2H), 2.66-2.49 (m, 2H), 2.49-2.22 (m, 4H), 2.17 (s, 1H), 2.07 (ddd, J=14.6, 10.3, 2.8 Hz, 1H), 1.91-1.77 (m, 2H), 1.76-1.62 (m, 2H), 1.54 (dd, J=13.0, 6.7 Hz, 1H), 1.41 (s, 8H), 1.24 (s, 2H), 1.05-0.79 (m, 6H). ESI MS m/z=488.02 [M−H]$^-$.

Example 2

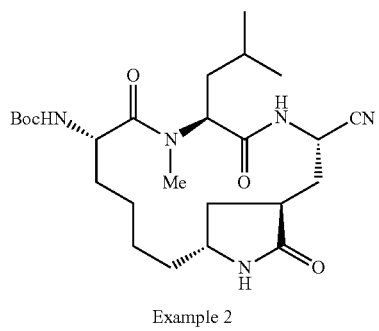

Example 2

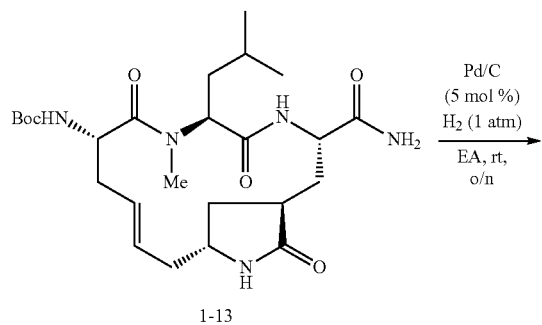

1-13

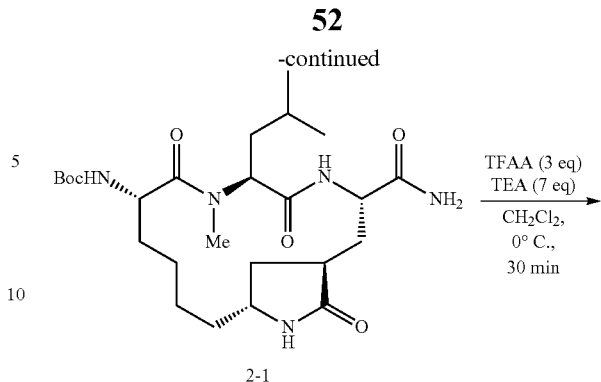

2-1

2-2: Example 2

Step 2-1: A solution of the compound from Step 1-13 (248 mg, 0.489 mmol) in ethyl acetate (5 ml) was treated with Pd—C (27 mg, 0.025 mmol) under H$_2$. The solution was bubbled with H$_2$ for 10 min. The reaction was stirred at room temperature overnight. The mixture was filtered through celite, rinsed with ethyl acetate and concentrated in vacuo to give the desired product (240 mg, 0.471 mmol, 96% yield) as a brownish solid. ESI MS m/z=508.09 [M−H]$^-$.

Step 2-2: A solution of the compound from Step 2-1 (170 mg, 0.334 mmol) in CH$_2$Cl2 (3 ml) was treated with TEA (270 μl, 1.937 mmol) and TFAA (150 μl, 1.062 mmol) dropwise at 0° C. The reaction was stirred at 0° C. for 30 min and quenched with a saturated solution of sodium bicarbonate. The mixture was stirred at room temperature overnight. The aqueous layer was extracted with dichloromethane over 3 times. The combined organic layer was dried over sodium sulfate, filtered and concentrated in vacuo. The crude was added to a 12 g silica gel column and eluted by methanol/dichloromethane from 0% to 20% to give the desired product Example 2 (111 mg, 0.226 mmol, 68% yield) as an off-white solid.

$^1$H NMR (400 MHz, Methanol-d$_4$) δ 5.17 (dd, J=10.4, 5.4 Hz, 1H), 4.95 (dd, J=13.0, 3.7 Hz, 1H), 4.52 (dd, J=11.2, 3.3 Hz, 1H), 3.63 (d, J=8.0 Hz, 1H), 3.24 (s, 2H), 2.50-2.31 (m, 2H), 1.98-1.89 (m, 1H), 1.89-1.79 (m, 3H), 1.74 (ddd, J=13.6, 11.9, 3.6 Hz, 1H), 1.58-1.41 (m, 7H), 1.41 (s, 7H), 1.28 (s, 1H), 1.26-1.21 (m, 3H), 1.19 (s, 2H), 0.97 (d, J=6.5 Hz, 3H), 0.89 (d, J=6.4 Hz, 3H). ESI MS m/z=490.07 [M−H]$^-$.

Example 3

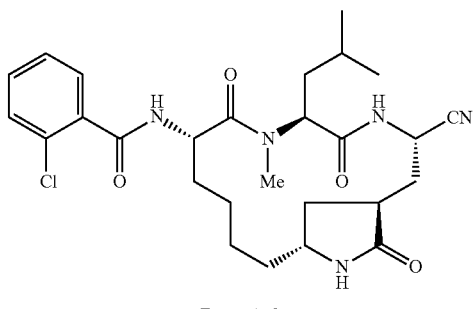

Example 3

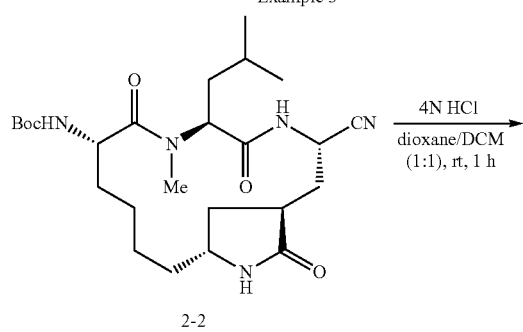

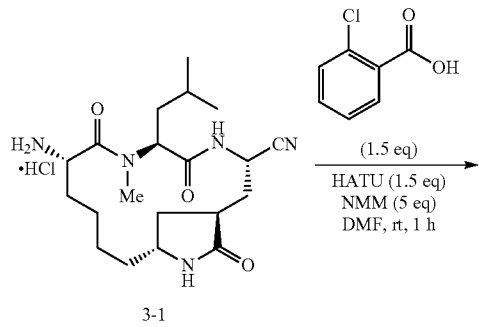

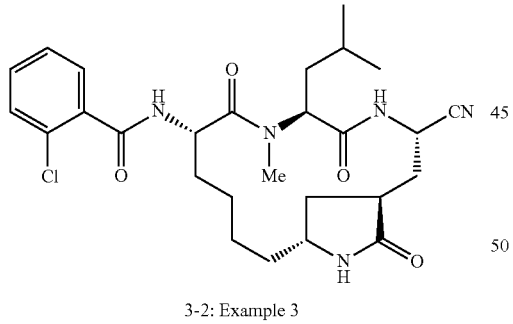

3-2: Example 3

Step 3-1: A solution of the compound from Step 2-2 (43 mg, 0.084 mmol) in CH₂Cl2 (0.2 ml) was treated with a 4 N HCl (0.2 ml, 0.800 mmol) in 1,4-Dioxane (0.200 ml). The reaction was stirred at room temperature for 1 h. The mixture was concentrated in vacuo and dried under high vacuum to give the desired product (38 mg, 0.084 mmol, 100% yield) as an off-white solid. ESI MS m/z=391.93 [M+H]$^+$.

Step 3-2: A solution of the compound from Step 3-1 (17 mg, 0.040 mmol) and 2-chlorobenzoic acid (12 mg, 0.077 mmol) in DMF (0.3 ml) was treated with N-methylmorpholine (30 μl, 0.273 mmol) and HATU (22 mg, 0.058 mmol). The reaction was stirred at room temperature for 1 h. The mixture was quenched with a saturated solution of sodium bicarbon- ate and diluted with ethyl acetate. The organic layer was washed with water and brine, dried over sodium sulfate, filtered and concentrated in vacuo. The crude product was added to a 4 g silica gel column and eluted by methanol/ dichloromethane from 0% to 20% to give Example 3 (12 mg, 0.023 mmol, 57% yield) as a white solid.

$^1$H NMR (500 MHz, Methanol-d$_4$) δ 7.50-7.33 (m, 5H), 5.20 (dd, J=10.4, 5.5 Hz, 1H), 5.07-4.94 (m, 2H), 3.67 (ddd, J=9.2, 6.2, 3.5 Hz, 1H), 3.35 (s, 2H), 2.52-2.32 (m, 3H), 2.12-1.94 (m, 3H), 1.94-1.83 (m, 2H), 1.82-1.67 (m, 3H), 1.66-1.46 (m, 6H), 1.35-1.26 (m, 2H), 1.24 (d, J=11.1 Hz, 2H), 1.07-0.85 (m, 8H). ESI MS m/z=528.00, 530.01 [M−H]$^-$.

Example 4

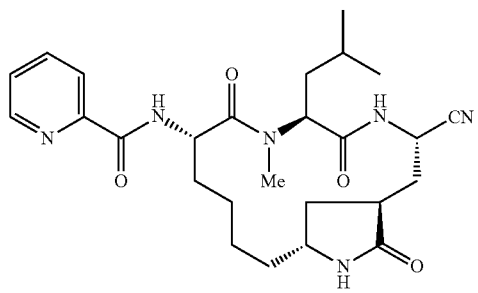

Example 4

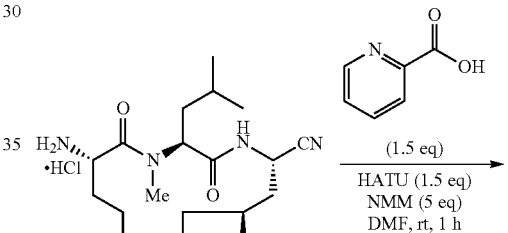

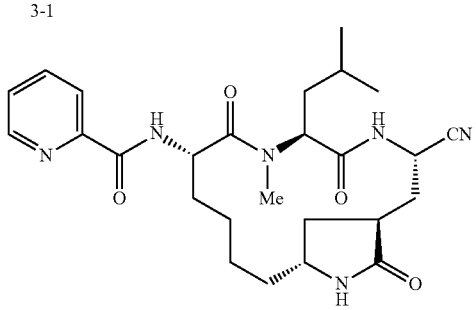

4-1: Example 4

Step 4-1: A solution of the compound from Step 3-1 (17 mg, 0.040 mmol) and picolinic acid (7 mg, 0.057 mmol) in DMF (0.3 ml) was treated with N-methylmorpholine (40 μl, 0.364 mmol) and HATU (24 mg, 0.063 mmol). The reaction was stirred at room temperature for 1 h. The mixture was quenched with a saturated solution of sodium bicarbonate and diluted with ethyl acetate. The organic layer was washed with water and brine, dried over sodium sulfate, filtered and concentrated in vacuo. The crude product was added to a 4 g silica gel column and eluted by methanol/dichloromethane from 0% to 20% to give Example 4 (11 mg, 0.022 mmol, 56% yield) as a white solid.

$^1$H NMR (500 MHz, Methanol-d$_4$) δ 8.69-8.57 (m, 1H), 8.13-8.04 (m, 1H), 8.01-7.91 (m, 1H), 7.61-7.51 (m, 1H), 5.19 (dd, J=9.6, 6.1 Hz, 1H), 5.09 (dd, J=10.5, 3.3 Hz, 1H), 4.99 (dd, J=13.1, 3.7 Hz, 1H), 3.67 (dq, J=10.9, 5.8, 5.3 Hz, 1H), 3.25 (d, J=5.3 Hz, 1H), 2.55-2.33 (m, 2H), 2.14-2.04 (m, 1H), 2.03-1.93 (m, 1H), 1.93-1.73 (m, 3H), 1.66-1.44 (m, 5H), 1.38-1.21 (m, 4H), 1.06-0.92 (m, 3H), 0.91-0.80 (m, 3H). ESI MS m/z=494.95 [M−H]$^-$.

5.07-4.95 (m, 2H), 3.72-3.65 (m, 1H), 3.33 (s, 7H), 3.31-3.23 (m, 8H), 2.63 (s, 1H), 2.55-2.34 (m, 2H), 2.17 (d, J=9.5 Hz, 4H), 2.13-2.03 (m, 1H), 2.03-1.69 (m, 6H), 1.68-1.51 (m, 5H), 1.42 (d, J=7.7 Hz, 1H), 1.28 (d, J=5.5 Hz, 2H), 1.25 (s, 4H), 1.06-0.89 (m, 4H), 0.88 (d, J=5.9 Hz, 3H). ESI MS m/z=586.94 [M−H]$^-$.

Example 5

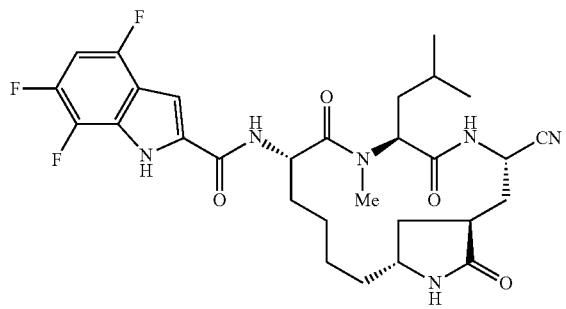

Example 5

Example 6

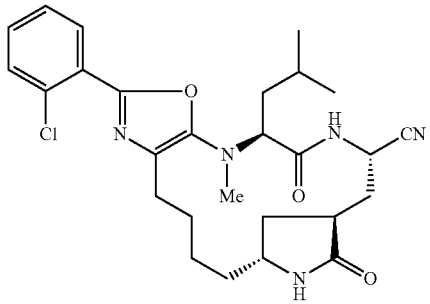

Example 6

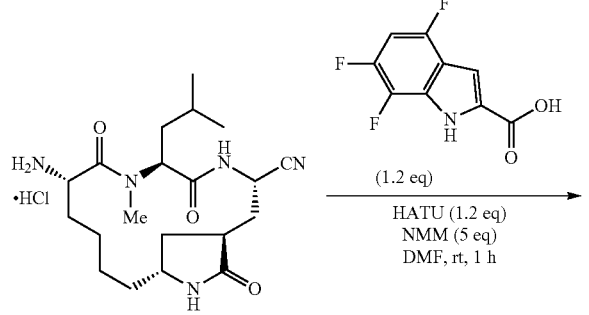

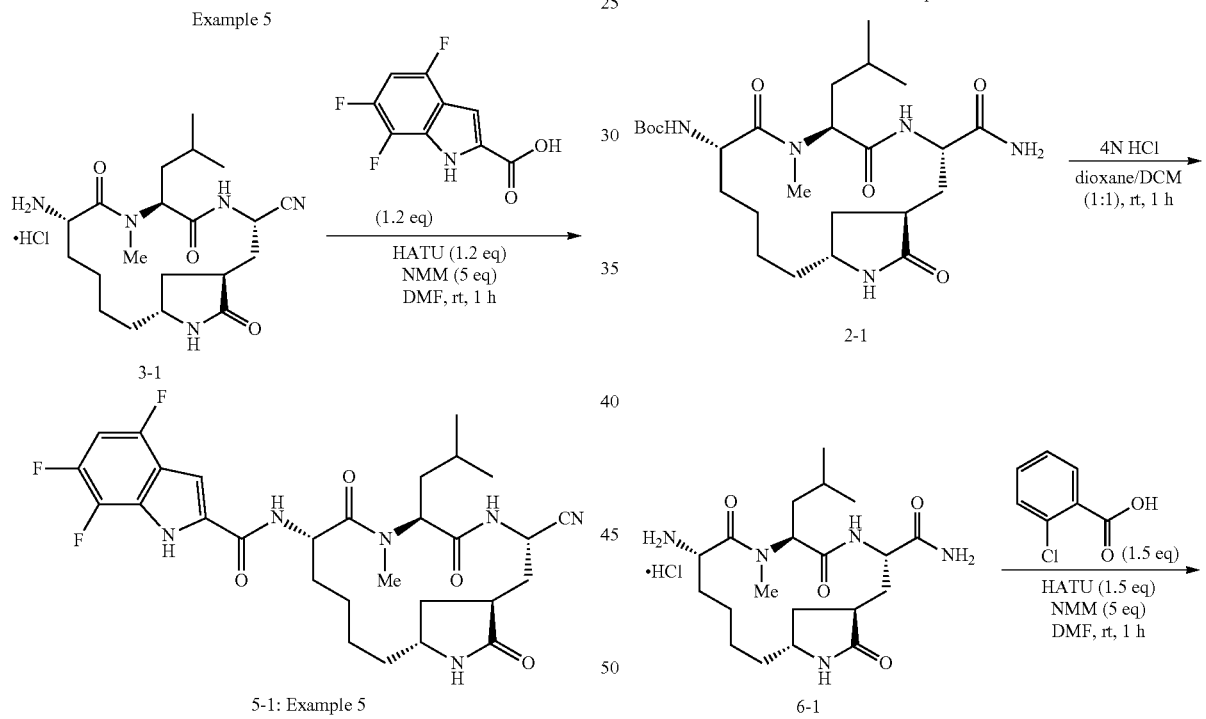

Step 5-1: A solution of the compound fro Step 3-1 (17 mg, 0.040 mmol) and 4,6,7-trifluoro-1H-indole-2-carboxylic acid (10 mg, 0.046 mmol) in DMF (0.3 ml) was treated with N-methylmorpholine (40 μl, 0.364 mmol) and HATU (18 mg, 0.047 mmol). The reaction was stirred at room temperature for 1 h. The reaction was diluted with ethyl acetate and quenched with a saturated solution of sodium bicarbonate. The organic layer was washed with brine and water, dried over sodium sulfate, filtered and concentrated in vacuo. The crude was added to a 4 g silica gel column and eluted by acetone/cyclohexane from 0% to 100% to give Example 5 (8 mg, 0.014 mmol, 34% yield) as a white solid.

$^1$H NMR (400 MHz, Methanol-d$_4$) δ 7.24 (t, J=2.9 Hz, 1H), 6.80 (ddd, J=11.2, 9.5, 5.2 Hz, 1H), 5.25-5.15 (m, 1H),

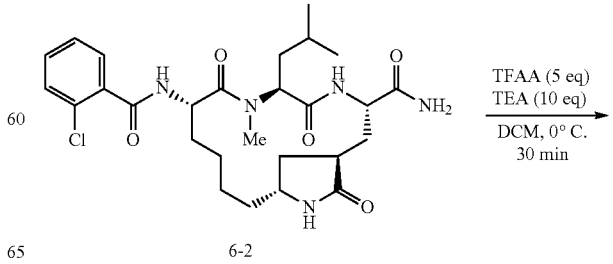

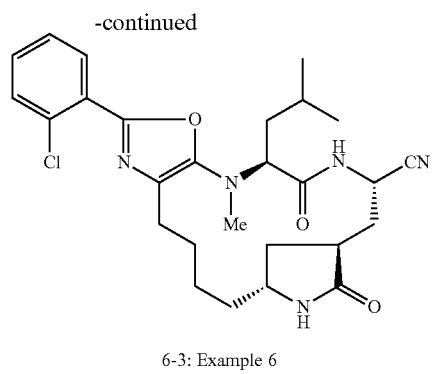

6-3: Example 6

Step 6-1: A solution of the compound from Step 2-1 (43 mg, 0.084 mmol) in CH$_2$Cl2 (0.2 ml) was treated with a 4 N HCl (0.2 ml, 0.800 mmol) in 1,4-Dioxane (0.200 ml). The reaction was stirred at room temperature for 1 h. The mixture was concentrated in vacuo. The mixture was treated with 1 ml dichloromethane and concentrated in vacuo again to give the desired product (38 mg, 0.084 mmol, 100% yield) as an off-white solid. ESI MS m/z=409.96 [M+H]$^+$.

Step 6-2: A solution of the compound from Step 6-1 (38 mg, 0.085 mmol) and 2-chlorobenzoic acid (20 mg, 0.128 mmol) in DMF (0.5 ml) was treated with N-methylmorpholine (50 μl, 0.455 mmol) and HATU (52 mg, 0.137 mmol). The reaction was stirred at room temperature for 30 min. The mixture was diluted with ethyl acetate and quenched with a saturated solution of sodium bicarbonate. The organic layer was washed with water and brine over 3 times, dried over sodium sulfate, filtered and concentrated in vacuo. The crude was added to a 4 g silica gel column and eluted by ethanol/dichloromethane from 0% to 20% to give the desired product (23 mg, 0.042 mmol, 49% yield) as a white solid.

$^1$H NMR (400 MHz, Methanol-d$_4$) δ 7.49-7.31 (m, 4H), 5.26 (dd, J=10.6, 5.1 Hz, 1H), 5.02 (dd, J=11.2, 3.2 Hz, 1H), 4.44 (dd, J=13.0, 3.5 Hz, 1H), 3.74-3.62 (m, 1H), 3.33 (d, J=6.6 Hz, 3H), 2.50 (tdd, J=11.8, 8.4, 3.5 Hz, 1H), 2.26-2.13 (m, 2H), 2.13-1.97 (m, 2H), 1.97-1.82 (m, 2H), 1.81-1.70 (m, 1H), 1.70-1.64 (m, 1H), 1.64-1.46 (m, 5H), 1.44-1.23 (m, 5H), 0.93 (dd, J=26.2, 6.1 Hz, 7H). ESI MS m/z=547.97, 549.83 [M+H]$^+$.

Step 6-3: A solution of the compound from Step 6-2 (22 mg, 0.040 mmol) in CH$_2$Cl2 (0.3 ml) was treated with TEA (50 μl, 0.359 mmol) and TFAA (20 μl, 0.142 mmol) dropwise at 0° C. The reaction was stirred at 0° C. for 1 h and quenched with a saturated solution of sodium bicarbonate. The mixture was stirred at room temperature overnight. The aqueous layer was extracted with dichloromethane over 3 times. The combined organic layer was dried over sodium sulfate, filtered and concentrated in vacuo. The crude product was added to a 4 g silica gel column and eluted by methanol/dichloromethane from 0% to 20% to the desired product (8 mg, 0.016 mmol, 39% yield) as a white solid.

$^1$H NMR (500 MHz, Methanol-d$_4$) δ 7.90-7.78 (m, 1H), 7.60-7.50 (m, 1H), 7.51-7.35 (m, 2H), 5.00 (dd, J=12.7, 3.2 Hz, 1H), 4.72 (dd, J=9.9, 5.1 Hz, 1H), 4.12-3.99 (m, 1H), 3.73-3.63 (m, 1H), 3.01 (d, J=49.8 Hz, 3H), 2.71-2.55 (m, 2H), 2.47-2.20 (m, 3H), 2.18 (s, 1H), 2.12-1.31 (m, 12H), 1.31-1.22 (m, 1H), 1.08-0.87 (m, 6H). ESI MS m/z=512.13, 513.92 [M+H]$^+$.

Biological Activity

SARS-CoV-2 3C-like (3CL) protease fluorescence assay (FRET): Recombinant SARS-CoV-2 3CL-protease was expressed and purified. TAMRA-SITSAVLQSGFRKMK-Dabcyl-OH peptide 3CLpro substrate was synthesized. Black, low volume, round-bottom, 384 well microplates were used. In a typical assay, 0.85 μL of test compound was dissolved in DMSO then incubated with SARS-CoV-2 3CL-protease (10 nM) in 10 μL assay buffer (50 mM HEPES [pH 7.5], 1 mM DTT, 0.01% BSA, 0.01% Triton-X 100) for 30 min at RT. Next, 10 μL of 3CL-protease substrate (40 μM) in assay buffer was added and the assays were monitored continuously for 1 h in an Envision multimode plate reader operating in fluorescence kinetics mode with excitation at 540 nm and emission at 580 nm at RT. No compound (DMSO only) and no enzyme controls were routinely included in each plate. All experiments were run in duplicate. Data Analysis: SARS-CoV-2 3CL-protease enzyme activity was measured as initial velocity of the linear phase (RFU/s) and normalized to controlled samples DMSO (100% activity) and no enzyme (0% activity) to determine percent residual activity at various concentrations of test compounds (0-10 μM). Data were fitted to normalized activity (variable slope) versus concentration fit in GraphPad Prism 7 to determine IC$_{50}$. All experiments were run in duplicate, and IC$_{50}$ ranges are reported as follows: A <0.1 μM; B 0.1-1 μM; C >1 μM.

SARS-CoV-2 Cellular Assay (Vero 76): Test compounds are serially diluted using eight half-log dilutions in test medium (MEM supplemented with 2% FBS and 50 μg/mL gentamicin). Each dilution is added to 5 wells of a 96-well plate with 80-100% confluent Vero 76 cells. Three wells of each dilution are infected with virus (SARS-CoV-2 USA-WA1/2020), and two wells remain uninfected as toxicity controls. Six wells are infected and untreated as virus controls, and six wells are uninfected and untreated as cell controls. Viruses are prepared to achieve the lowest possible multiplicity of infection (MOI ~0.002) that would yield >80% cytopathic effect (CPE) at 6 days. Plates are incubated at 37±2° C., 5% CO$_2$. For neutral red assay, on day 6 post-infection, once untreated virus control wells reach maximum CPE, plates are stained with neutral red dye for approximately 2 hours (15 minutes). Supernatant dye is removed, and wells are rinsed with PBS, and the incorporated dye is extracted in 50:50 Sorensen citrate buffer/ethanol for >30 minutes and the optical density is read on a spectrophotometer at 540 nm. Optical densities are converted to percent of cell controls and normalized to the virus control, then the concentration of test compound required to inhibit CPE by 50% (EC$_{50}$) is calculated by regression analysis. The concentration of compound that would cause 50% cell death in the absence of virus was similarly calculated (CC$_{50}$). EC$_{50}$ ranges are reported as follows: A <1 μM; B 1-10 μM; C >10 μM. CC$_{50}$ ranges are reported as follows: A <1 μM; B 1-50 μM; C >50 μM.

229E Cellular Assay (MRC5): EC$_{50}$ ranges are reported as follows: A <0.1 M; B 0.1-1 μM; C >1 μM.

Viral stock preparation: MRC-5 cells, (a diploid cell culture line composed of fibroblasts, originally developed from the lung tissue of a 14-week-old aborted Caucasian male fetus), were used for the culturing of 229E human corona virus (hCoV). Flasks were inoculated with hCoV-229E and viral stocks were collected once cytopathic effect (CPE) was greater than 70%. Viral stocks in Growth Media (EMEM, 1% Penn/Strep, 1% nonessential amino acids, 10% heat-inactivated FBS) plus 5% glycerol were snap frozen using liquid nitrogen and stored at −80° C. Viral stock titers were quantified by a $TCID_{50}$ (50% median tissue culture infectious dose) assay, as described elsewhere.

229E live virus assay: 384-well black cell-culture-treated plastic clear-bottom plates are used in this assay. Using an ECHO liquid dispenser, 3-fold serial dilutions of control and test compounds suspended in DMSO are added to the plate wells in duplicate in a total volume of 125 nL per well. MRC-5 cells below passage 17 are seeded into the inner 240 wells of the 384-well plate at 1,500 cells per well in a volume of 12.5 µL using Growth Media. Viral stock is then added to the wells at a multiplicity of infection (MOI) of 0.05 in a volume of 12.5 µL per well, bringing the total volume of each well to ~25 µL. Each plate has a control row of 20 wells with cells plus DMSO and virus but no compound (positive control, max CPE, minimum ATPlite signal), and a row with cells plus DMSO but no compound or virus (negative control, minimum CPE, maximum ATPlite signal), and a row with no cells or virus or compound (background plate/reagent control). The control wells with cells but no virus are given an additional 12.5 µL of growth media containing an equal quantity of glycerol as those wells receiving the viral stock in order to keep consistent in media and volume conditions. The outer 2 rows/columns of wells are filled with 30 µL of moat media (DMEM, 1% Penn/Strep) to act as a thermal and evaporative barrier around the test wells. Following addition of all components, the sides of the plates are gently tapped by hand to promote even cell distribution across the wells. Upon confirmation of cell distribution, plates are incubated at 34° C. in a $CO_2$ humidity-controlled incubator for 6 days. Following the 6-day incubation period, the plates are read using ATPlite (12.5 µL added per well), which quantifies the amount of ATP (a measure of cell health) present in each well. Assay plates are read using an Envision luminometer. These data are used to calculate the percent cell health per well relative to the negative control wells and the $EC_{50}$ of each compound is calculated using ExcelFit software and 4-parameter logistical curve fitting analysis. $EC_{50}$ ranges are reported as follows: A <0.1 µM; B 0.1-1 µM; C >1 µM.

TABLE 1

Summary of Activities

| Example # | $EC_{50}$ (229E) | FRET $IC_{50}$ |
|---|---|---|
| 1 | C | B |
| 2 | C | A |
| 3 | B | A |
| 4 | C | A |
| 5 | C | B |
| 6 | B | B |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Formula (III), or a pharmaceutically acceptable salt thereof:

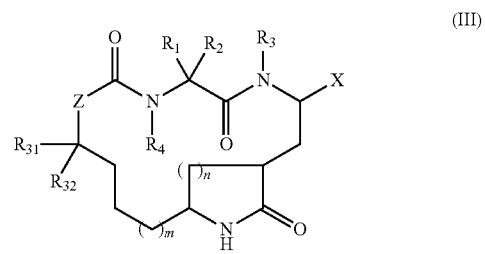

wherein
  m is 1;
  n is 1;
  X is selected from the group consisting of —CN, —C(O)C(O)NR$_{13}$R$_{14}$, and —C≡R$_{13}$;
  R$_1$ and R$_2$ are each independently hydrogen or C$_1$-C$_6$-alkyl;
  R$_3$ and R$_4$ are each independently hydrogen or C$_1$-C$_4$-alkyl;
  Z is —CR$_{21}$R$_{23}$-, or Z and the oxygen atom of the carbonyl group are taken together with the carbon atom to which they are attached to form an optionally substituted heteroaryl;
  R$_{21}$ is selected from the group consisting of hydrogen, halogen, optionally substituted —C$_1$-C$_6$ alkyl, and optionally substituted —C$_3$-C$_8$ cycloalkyl;
  R$_{23}$ is selected from the group consisting of hydrogen, halogen, —OH, —OR$_{15}$, —OC(O)R$_{15}$, —OC(O)OR$_{15}$, —OC(O)NR$_{13}$R$_{14}$, —NR$_{13}$R$_{18}$, —N$_3$, —CN, optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocycloalkyl, optionally substituted aryl, optionally substituted arylalkyl, optionally substituted heteroaryl, and optionally substituted heteroarylalkyl;
  R$_{13}$ and R$_{14}$ are independently selected from the group consisting of hydrogen, optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocycloalkyl, optionally substituted aryl, optionally substituted arylalkyl, optionally substituted heteroaryl, optionally substituted heteroarylalkyl; alternatively R$_{13}$ and R$_{14}$ are taken together with the nitrogen atom to which they are attached to form an optionally substituted 3- to 8-membered heterocyclic ring;
  R$_{15}$ is selected from the group consisting of optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocycloalkyl, optionally substituted aryl, optionally substituted arylalkyl, optionally substituted heteroaryl, and optionally substituted heteroarylalkyl;
  R$_{18}$ is selected from the group consisting of hydrogen, optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocycloalkyl, optionally substituted aryl, optionally substituted arylalkyl, optionally substituted heteroaryl, optionally substituted heteroarylalkyl, —C(O)R$_{15}$, —C(O)OR$_{15}$, —C(O)NR$_{13}$R$_{14}$, —C(O)C(O)NR$_{13}$R$_{14}$, —S(O)$_2$R$_{15}$, and —S(O)$_2$NR$_{13}$R$_{14}$; and R$_{31}$ and R$_{32}$ are both hydrogen.

2. The compound of claim 1, wherein Z is

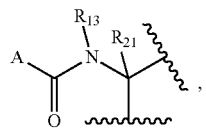

wherein A is selected from the group consisting of —R$_{15}$, —OR$_{15}$, —NR$_{13}$R$_{14}$, and —C(O)NR$_3$R$_{14}$; R$_{15}$ is selected from the group consisting of optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocycloalkyl, optionally substituted aryl, optionally substituted arylalkyl, optionally substituted heteroaryl, and optionally substituted heteroarylalkyl; and R$_{13}$, R$_{14}$, R$_{15}$, and R$_{21}$ are as defined in claim 1.

3. The compound of claim 1, represented by Formula (VI-1) or Formula (VI-3), or a pharmaceutically acceptable salt thereof:

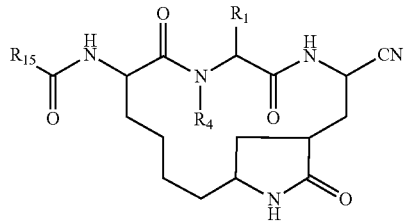

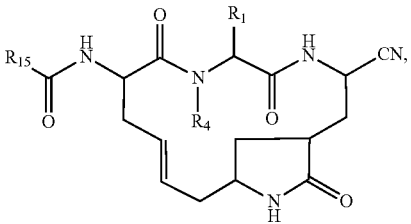

wherein R$_1$, R$_4$, and R$_{15}$ are as defined in claim 1.

4. The compound of claim 1, selected from the compounds set forth below, or a pharmaceutically acceptable salt thereof:

| Compound | Structure |
|---|---|
| 1 | 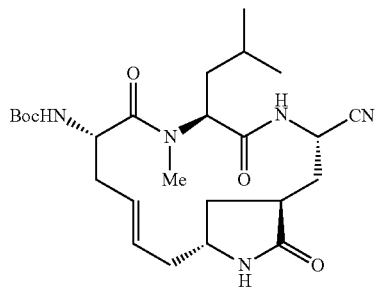 [SMILES: CC(C)C[C@H]1C(=O)N[C@H](C#N)C[C@@H]2C[C@@H](C/C=C/C[C@H](NC(=O)OC(C)(C)C)C(=O)N1C)NC2=O] |
| 2 | 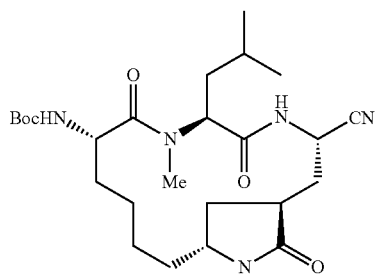 |
| 3 | 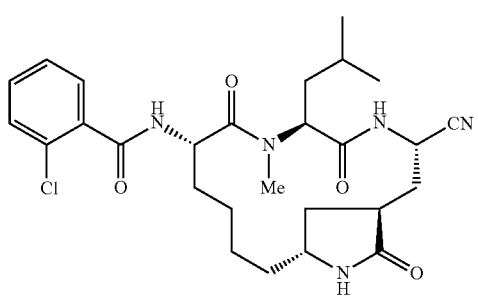 [SMILES: CC(C)C[C@H]1C(=O)N[C@H](C#N)C[C@@H]2C[C@@H](CCCC[C@H](NC(=O)c3ccccc3Cl)C(=O)N1C)NC2=O] |

| Compound | Structure |
|---|---|
| 4 | 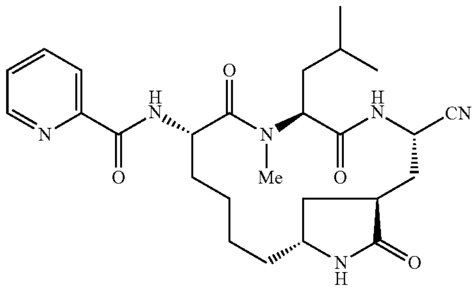 [SMILES: CC(C)C[C@H]1C(=O)N[C@H](C#N)C[C@@H]2C[C@@H](CCCC[C@H](NC(=O)c3ccccn3)C(=O)N1C)NC2=O] |
| 5 | 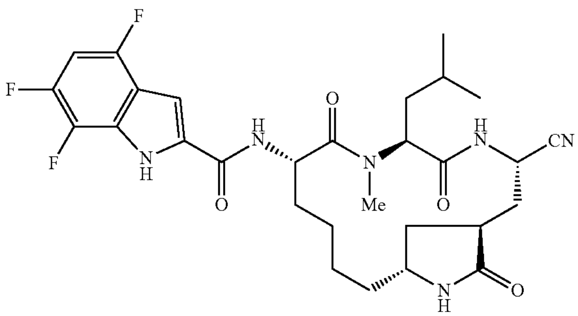 [SMILES: CC(C)C[C@H]1C(=O)N[C@H](C#N)C[C@@H]2C[C@@H](CCCC[C@H](NC(=O)c3cc4c(F)cc(F)c(F)c4[nH]3)C(=O)N1C)NC2=O] |
| 6 | 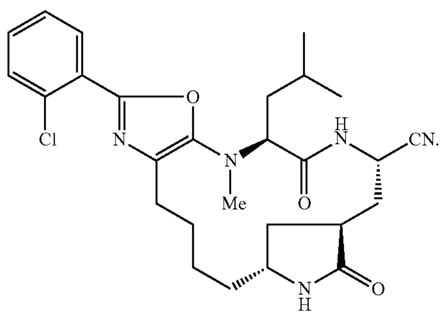 [SMILES: CC(C)C[C@H]1C(=O)N[C@H](C#N)C[C@@H]2C[C@@H](CCCCc3nc(-c4ccccc4Cl)oc3N1C)NC2=O] |

5. A pharmaceutical composition comprising a compound according to claim 1, or a pharmaceutically acceptable salt thereof, and a pharmaceutically acceptable carrier or excipient.

6. A method of treating a viral infection the method comprising administering to the subject a therapeutically effective amount of a compound according to claim 1, or a pharmaceutically acceptable salt thereof.

7. The method according to claim 6, wherein the subject is a human.

8. A method of treating a coronavirus infection in a subject in need thereof, comprising administering to the subject a therapeutically effective amount of a compound according to claim 1, or a pharmaceutically acceptable salt thereof.

9. A method according to claim 8, wherein the coronavirus is selected from a 229E, NL63, OC43, HKU1, SARS-CoV or a MERS coronavirus.

10. The method according to claim 8, wherein the compound is administered to the subject orally, subcutaneously, intravenously or by inhalation.

11. A method of inhibiting viral 3C protease or viral 3CL protease in a subject, comprising administering to said subject an effective amount of a compound according to claim 1, or a pharmaceutically acceptable salt thereof.

* * * * *